United States Patent
Ghosh et al.

(10) Patent No.: US 11,795,159 B2
(45) Date of Patent: Oct. 24, 2023

(54) COMPOUNDS FOR THE TREATMENT OF SARS

(71) Applicant: Purdue Research Foundation, West Lafayette, IN (US)

(72) Inventors: Arun K. Ghosh, West Lafayette, IN (US); Hiroaki Mitsuya, Kumamoto (JP); Andrew Mesecar, West Lafayette, IN (US); Dana Shahabi, West Lafayette, IN (US)

(73) Assignee: Purdue Research Foundation, West Lafayette, IN (US)

( * ) Notice: Subject to any disclaimer, the term of this patent is extended or adjusted under 35 U.S.C. 154(b) by 0 days.

(21) Appl. No.: 17/751,659

(22) Filed: May 23, 2022

(65) Prior Publication Data

US 2022/0411401 A1    Dec. 29, 2022

Related U.S. Application Data

(60) Provisional application No. 63/193,323, filed on May 26, 2021.

(51) Int. Cl.
| | | |
|---|---|---|
| *C07D 401/12* | (2006.01) | |
| *C07D 401/02* | (2006.01) | |
| *C07D 401/14* | (2006.01) | |
| *C07D 413/14* | (2006.01) | |
| *C07D 417/12* | (2006.01) | |
| *C07D 413/12* | (2006.01) | |

(52) U.S. Cl.
CPC ......... *C07D 401/12* (2013.01); *C07D 401/14* (2013.01); *C07D 413/12* (2013.01); *C07D 413/14* (2013.01); *C07D 417/12* (2013.01)

(58) Field of Classification Search
CPC ............................ C07D 401/12; C07D 401/02
See application file for complete search history.

(56) References Cited

FOREIGN PATENT DOCUMENTS

WO    WO-2021212039 A1 * 10/2021 ........... A61K 31/496

OTHER PUBLICATIONS

"U.S. Appl. No. 17/751,659, Preliminary Amendment Filed May 25, 2022", 3 pgs.
Abuchowski, Abraham, et al., "Chapter 13. Soluble Polymer-Enzyme Adducts", In: Enzymes as Drugs, Hocenberg and Roberts, eds., Wiley-Interscience, New York, N.Y., (1981), 367-383.
Berge, Stephen M, et al., "Pharmaceutical Salts", Journal of Pharmaceutical Sciences, 66(1), (Jan. 1977), 1-19.
Hattori, Shin-Ichiro, et al., "A small molecule compound with an indole moiety inhibits the main protease of SARS-COV-2 and blocks virus replication", Nature Communications, 12, Article No. 668, (2021), 1-21.
Hattori, Shin-Ichiro, et al., "GRL-0920, an Indole Chloropyridinyl Ester, Completely Blocks SARS-COV-2 Infection", mBio, vol. 11, No. 4, (2020), 1-16.
Langer, Robert, "New Methods of Drug Delivery", Science, 249(4976), (Sep. 1990), 1527-1533.
Newmark, J., et al., "Preparation and Properties of Adducts of Streptokinase and Streptokinase-Plasmin Complex with Polyethylene Glycol and Pluronic Polyol F38", J. of Applied Biochemistry, 4, (1982), 185-189.

* cited by examiner

*Primary Examiner* — Samira J Jean-Louis
(74) *Attorney, Agent, or Firm* — Schwegman Lundberg & Woessner, P.A.

(57) ABSTRACT

Bis-amide inhibitors of SARS-CoV-2 (COVID); pharmaceutical compositions comprising same; and methods of treating a severe acute respiratory syndrome.

9 Claims, No Drawings

COMPOUNDS FOR THE TREATMENT OF SARS

CROSS REFERENCE TO RELATED APPLICATIONS

This application claims priority to U.S. provisional patent application No. 63/193,323, which was filed on May 26, 2021, which is hereby incorporated by reference in its entirety.

STATEMENT OF U.S. GOVERNMENT SUPPORT

This invention was made with government support under contract numbers AI150466 and HHSN272201700060C awarded by the National Institutes of Health. The government has certain rights in the invention.

BACKGROUND

Coronaviruses (CoVs) are enveloped viruses with a positive-sense, single-stranded RNA and are associated with various natural hosts. CoVs are divided into alpha, beta, gamma, and delta groups, and the beta group is further composed of A, B, C, and D subgroups. Among them, six CoVs can infect humans (HCoVs), including HCoV-229E (229E) and HCoV-NL63 (NL63) in the alpha group, HCoV-OC43 (OC43) and HCoV-HKU1 (HKU1) in beta subgroup A, severe acute respiratory syndrome CoV (SARS-CoV) in beta subgroup B, and Middle East respiratory syndrome CoV (MERS-CoV) in beta subgroup C.

In this century, SARS-CoV and MERS-CoV have emerged in the human population and caused severe pulmonary disease with alarmingly high fatality rates. In 2002, SARS-CoV infections first appeared in China and then quickly spread as a global pandemic to more than 30 countries with 8,273 infections and 775 deaths (nearly 10% mortality). In 2012, MERS-CoV emerged in Saudi Arabia and spread throughout the Middle East. In 2015, the second outbreak of MERS-CoV occurred in South Korea, causing super-spreading events with third- and fourth-generation cases of infection. The World Health Organization has reported 2,229 laboratory-confirmed cases of MERS-CoV infection, including 791 deaths (about 35% case fatality) in 27 countries as of August 2018 (the worldwide web at who[dot]int/emergencies/mers-cov/en/). Meanwhile, the remaining common HCoVs, such as 229E, OC43, and NL63, usually infect the human upper respiratory tract and cause the common cold, but they also are responsible for severe and even fatal diseases in children, the elderly, and immunocompromised patients. These scenarios suggest that those common HCoVs might also pose a lethal threat to humans. Note that HCoVs are rapidly evolving. OC43 isolates with novel genomes are being continuously identified.

The ongoing outbreak of coronavirus disease (COVID-19) originated in China in December 2019 and became a global pandemic by March 2020. COVID-19 is caused by a novel coronavirus, severe acute respiratory syndrome-coronavirus 2 (SARS-CoV-2). Two other coronaviruses have caused worldwide outbreaks in the past two decades, namely SARS-CoV (2002-2003) and Middle East respiratory syndrome coronavirus (MERS-CoV) (2012-present). There is currently no treatment for COVID-19. Therefore, the development of a drug that could inhibit SARS-CoV-2 would address an urgent unmet medical need.

SUMMARY

The disclosure relates to a compound of Formula (I):

(I)

wherein:
$R^1$ is alkyl, cycloalkyl, heterocyclyl, 8-10-membered bicyclyl, or alkylene-aryl;
$R^2$ is substituted heterocyclyl;
$R^3$ is heterocyclyl; and
$R^4$ is substituted aryl;
or a pharmaceutically acceptable salt thereof.

The disclosure relates to a compound of Formula (I):

(I)

wherein:
$R^1$ is alkyl;
$R^2$ is substituted heterocyclyl;
$R^3$ is heterocyclyl; and
$R^4$ is substituted aryl;
or a pharmaceutically acceptable salt thereof.

The disclosure relates to a compound of Formula (I):

(I)

wherein:
$R^1$ is alkyl;
$R^2$ is or $R^{2a}$ is —C(O)alkyl, —C(O)alkenyl, or —S(O)$_2$-alkenyl
$R^3$ is heterocyclyl; and
$R^4$ is substituted aryl;
or a pharmaceutically acceptable salt thereof.

The disclosure also relates to a compound of Formula (II):

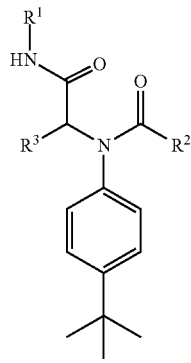

(II)

wherein:
$R^1$ is alkyl, cycloalkyl, heterocyclyl, 8-10-membered bicyclyl, or alkylene-aryl;
$R^2$ is substituted heterocyclyl; and
$R^3$ is heterocyclyl;
or a pharmaceutically acceptable salt thereof.

The disclosure also relates to a compound of Formula (III):

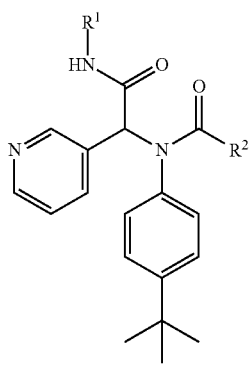

(III)

wherein:
$R^1$ is alkyl, cycloalkyl, heterocyclyl, 8-10-membered bicyclyl, or alkylene-aryl; and
$R^2$ is substituted heterocyclyl;
or a pharmaceutically acceptable salt thereof.

The disclosure further relates to a pharmaceutical composition comprising a therapeutically effective amount of one or more compounds and a pharmaceutically acceptable carrier.

The disclosure still further relates to a method for treating a severe acute respiratory syndrome. The method comprises administering a therapeutically effective amount of one or more compounds, or a pharmaceutical composition comprising same, to a patient in need thereof.

DETAILED DESCRIPTION

While the concepts of the present disclosure are illustrated and described in detail in the figures and descriptions herein, results in the figures and their description are to be considered as examples and not restrictive in character; it being understood that only the illustrative embodiments are shown and described and that all changes and modifications that come within the spirit of the disclosure are desired to be protected.

The disclosure relates to compounds that inhibit SARS-CoV-2. The compounds are useful for the treatment of severe acute respiratory system.

Compounds

The disclosure relates to a compound of Formula (I):

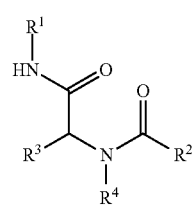

(I)

wherein:
$R^1$ is alkyl, cycloalkyl, heterocyclyl, 8-10-membered bicyclyl, or alkylene-aryl;
$R^2$ is substituted heterocyclyl;
$R^3$ is heterocyclyl; and
$R^4$ is substituted aryl;
or a pharmaceutically acceptable salt thereof.

The disclosure relates to a compound of Formula (I):

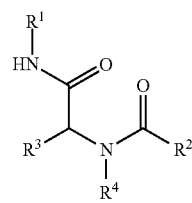

(I)

wherein:
$R^1$ is alkyl;
$R^2$ is substituted heterocyclyl;
$R^3$ is heterocyclyl; and
$R^4$ is substituted aryl;
or a pharmaceutically acceptable salt thereof.

The disclosure relates to a compound of Formula (I):

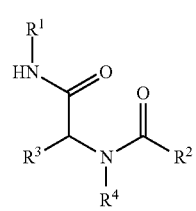

(I)

wherein:
$R^1$ is alkyl;
$R^2$ is

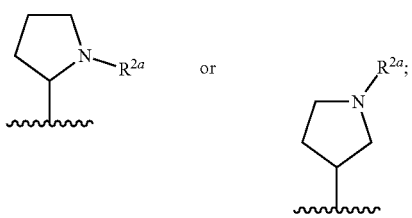 or 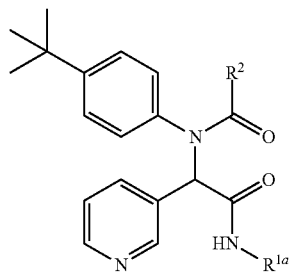

$R^{2a}$ is —C(O)alkyl, —C(O)alkenyl, or —S(O)$_2$-alkenyl
$R^3$ is heterocyclyl; and
$R^4$ is substituted aryl;
or a pharmaceutically acceptable salt thereof.

The disclosure relates to a compound of Formula (II):

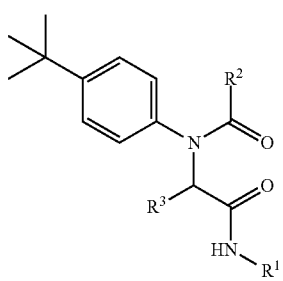

(II)

wherein:
$R^1$ is alkyl, cycloalkyl, heterocyclyl, 8-10-membered bicyclyl, or alkylene-aryl;
$R^2$ is substituted heterocyclyl; and
$R^3$ is heterocyclyl;
or a pharmaceutically acceptable salt thereof.

The disclosure also relates to a compound of Formula (III):

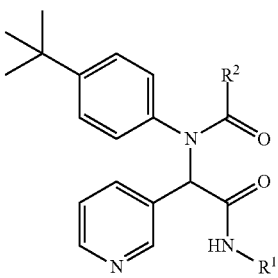

(III)

wherein:
$R^1$ is alkyl, cycloalkyl, heterocyclyl, 8-10-membered bicyclyl, or alkylene-aryl; and
$R^2$ is substituted heterocyclyl;
or a pharmaceutically acceptable salt thereof.

The compounds of Formula (III) can be compounds of Formula (IIIa):

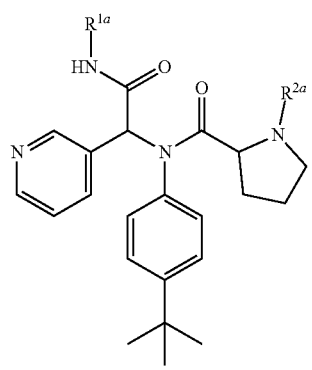

(IIIa)

wherein:
$R^{1a}$ is alkyl; and
$R^2$ is substituted heterocyclyl;
or a pharmaceutically acceptable salt thereof.

The compounds of Formula (III) can be compounds of Formula (IIIb) or (IIIc):

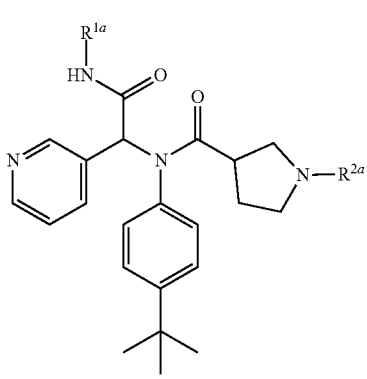

(IIIb)

(IIIc)

wherein:
$R^{1a}$ is alkyl; and
$R^{2a}$ is —C(O)alkyl, —C(O)alkenyl, or —S(O)$_2$-alkenyl;
or a pharmaceutically acceptable salt thereof.

$R^1$ can be alkyl. $R^1$ can be t-butyl. $R^1$ can be cycloalkyl. $R^1$ can be cyclopentyl. $R^1$ can be cyclohexyl. $R^1$ can be unsubstituted heterocyclyl. $R^1$ can be substituted heterocyclyl. $R^1$ can be an unsubstituted 8-10-membered bicyclyl. $R^1$ can be a substituted 8-10-membered bicyclyl. $R^1$ can be unsubstituted alkylene-aryl. $R^1$ can be substituted alkylene-aryl.

R¹ can be
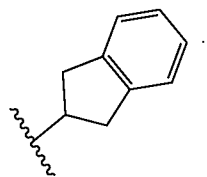 [SMILES: *C1Cc2ccccc2C1]
R¹ can be
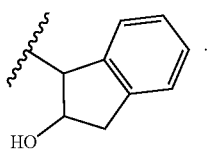 [SMILES: *C1c2ccccc2CC1O]
R¹ can be
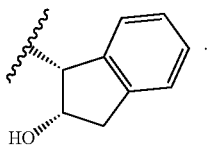 [SMILES: *[C@@H]1c2ccccc2C[C@@H]1O]
R¹ can be
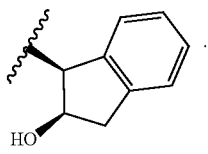 [SMILES: *[C@H]1c2ccccc2C[C@H]1O]
R¹ can be
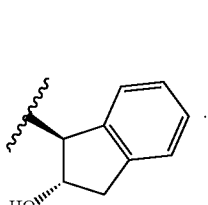
R¹ can be
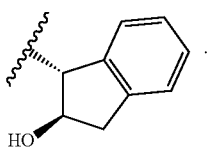 [SMILES: *[C@@H]1c2ccccc2C[C@H]1O]
R¹ can be
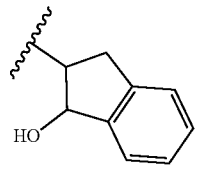
R¹ can be
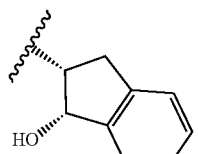
R¹ can be
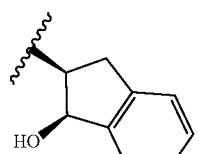
R¹ can be
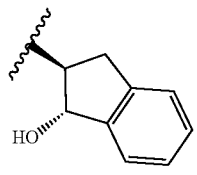
R¹ can be
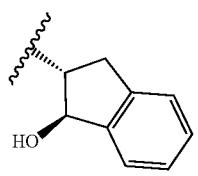

R¹ can be
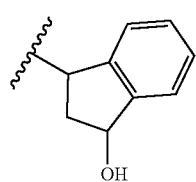
R¹ can be
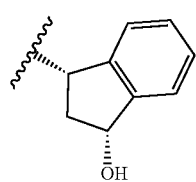
R¹ can be
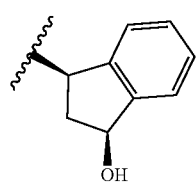
R¹ can be
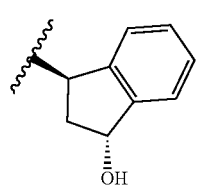
R¹ can be
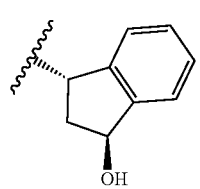
R¹ can be
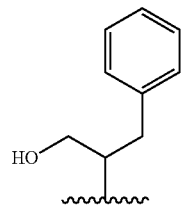
R¹ can be
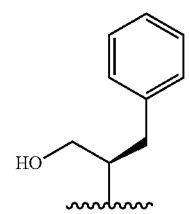 [SMILES: *[C@@H](CO)Cc1ccccc1]
R¹ can be
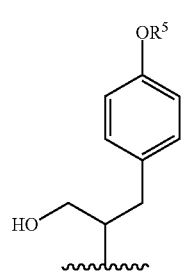
R¹ can be
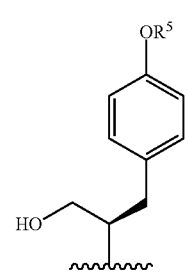

R¹ can be
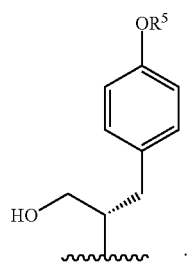
R¹ can be
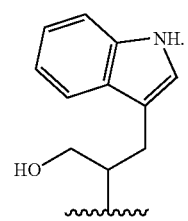 [SMILES: *C(CO)Cc1c[nH]c2ccccc12]
R¹ can be
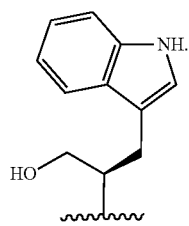 [SMILES: *[C@@H](CO)Cc1c[nH]c2ccccc12]
R¹ can be
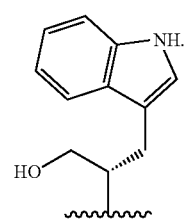 [SMILES: *[C@H](CO)Cc1c[nH]c2ccccc12]
R¹ can be
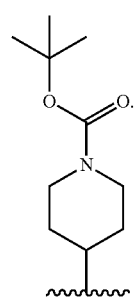
R¹ can be
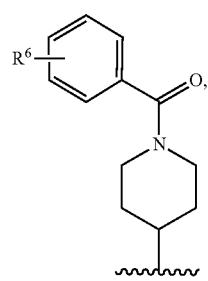
wherein $R^5$ is H or $C_{1-4}$alkyl, and $R^6$ is H, F, Cl, —OMe, —NH$_2$, or —N(H)Me. R¹ can be
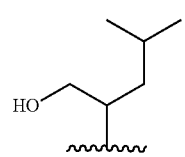
R¹ can be
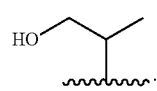
$R^{1a}$ can be t-butyl.
In combination with the foregoing R¹ and $R^{1a}$ groups:
R² can be
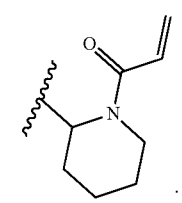 [SMILES: *C1CCCCN1C(=O)C=C]
R² can be
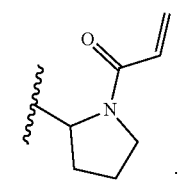 [SMILES: *C1CCCN1C(=O)C=C]

$R^2$ can be
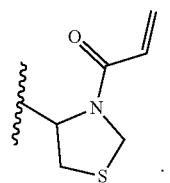 [SMILES: *C1CSCN1C(=O)C=C]
$R^2$ can be
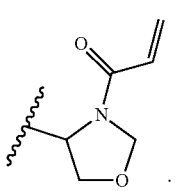
$R^2$ can be
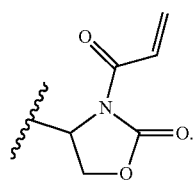 [SMILES: *C1COC(=O)N1C(=O)C=C]
$R^2$ can be
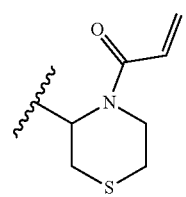
$R^2$ can be
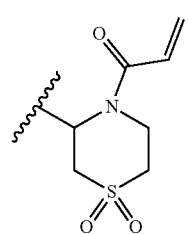
$R^2$ can be
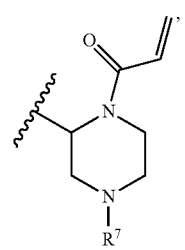
wherein $R^7$ can be H, ME, or Boc. $R^2$ can be
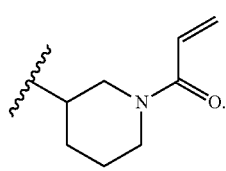 [SMILES: *C1CCCN(C(=O)C=C)C1]
$R^2$ can be
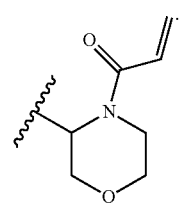 [SMILES: *C1COCCN1C(=O)C=C]
$R^2$ can be
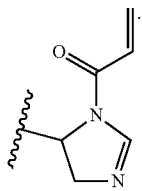 [SMILES: *C1CN=CN1C(=O)C=C]
$R^2$ can be
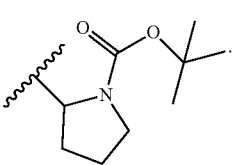 [SMILES: *C1CCCN1C(=O)OC(C)(C)C]

R² can be

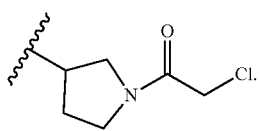 [SMILES: *C1CCN(C(=O)CCl)C1]

R² can be

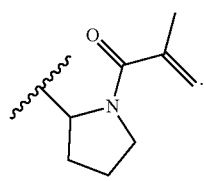 [SMILES: *C1CCCN1C(=O)C(=C)C]

R² can be

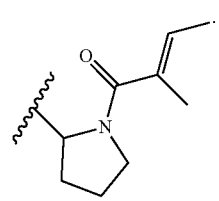 [SMILES: *C1CCCN1C(=O)/C(C)=C/C]

R² can be

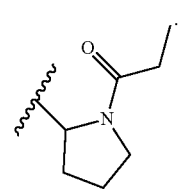 [SMILES: *C1CCCN1C(=O)CC]

R² can be

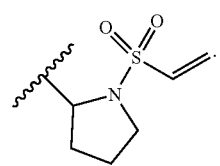 [SMILES: *C1CCCN1S(=O)(=O)C=C]

R² can be

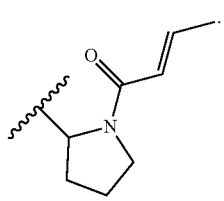 [SMILES: *C1CCCN1C(=O)/C=C/C]

In combination with the foregoing $R^{1a}$ groups:
$R^{2a}$ can be

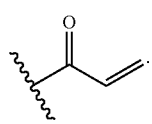

$R^{2a}$ can be

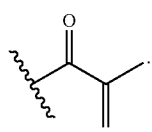

$R^{2a}$ can be

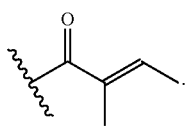 [SMILES: *C(=O)/C(C)=C/C]

$R^{2a}$ can be

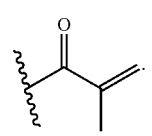 [SMILES: *C(=O)C(=C)C]

$R^{2a}$ can be

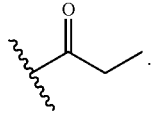 [SMILES: *C(=O)CC]

$R^{2a}$ can be

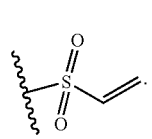

In combination with at least one of the foregoing $R^1$ and $R^2$ groups $R^3$ can be unsubstituted heteroaryl.
$R^3$ can be

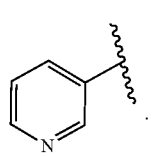

In combination with at least one of the foregoing $R^1$, $R^2$, and $R^3$ groups $R^4$ can be substituted phenyl.

R⁴ can be

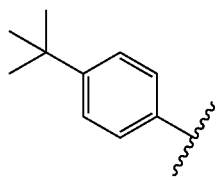

R⁴ can be

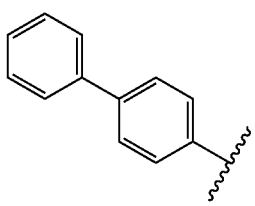

R⁴ can be

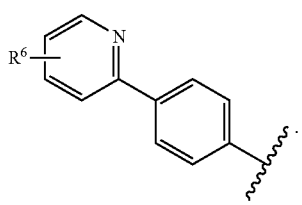

R⁴ can be

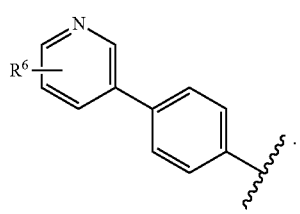

R⁴ can be

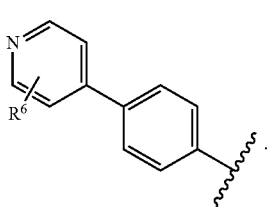

R⁶ is H, F, Cl, —OMe, —NH₂, or —N(H)Me.

Alkyl, alkylene, aryl, cycloalkyl, heterocyclyl, and bicyclyl can be substituted with one or more groups selected from alkyl, aryl, heterocyclyl, halo, hydroxy, alkoxy, amino, nitro, sulfhydryl, imino, amido, sulfamoyl, sulfinyl, alkylthio, sulfonyl, ketone, a heterocyclyl, an aromatic or heteroaromatic moiety, —CN, —NO₂, —C(O)₂-alkyl, —C(O)NH₂, —N(H)CO-alkyl, —N(H)-alkylene-aryl, —C(F₂)CH₃, —CF₃, or —C(F)H₂. If a moiety is substituted with two or more substituents, the substituents can be the same or different. Two substituents can be taken together to form a ring.

The compound of formula (I) can be selected from:

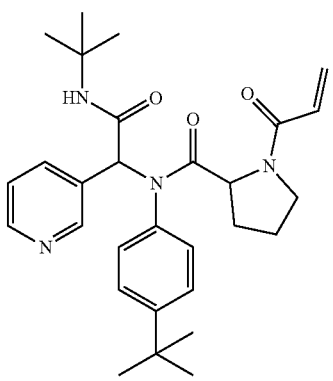

(D-proline), 1

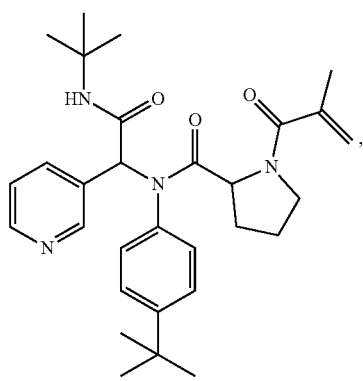

2

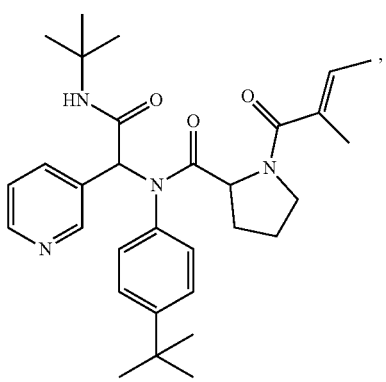

3

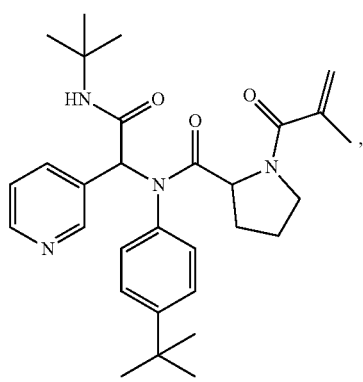

4

5
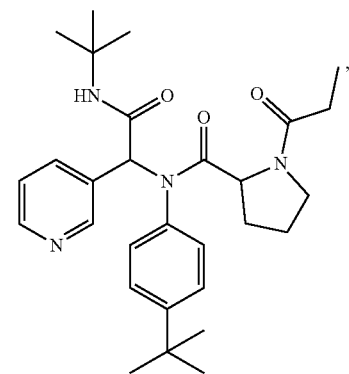
6
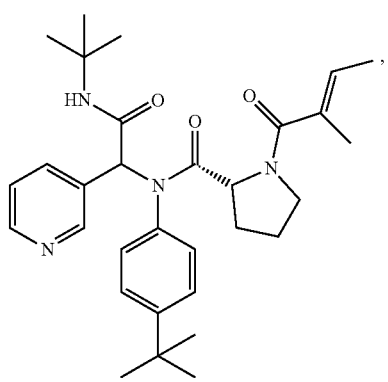
7
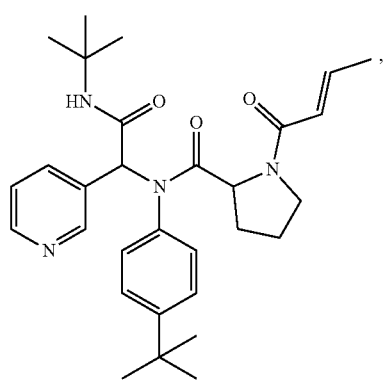
8
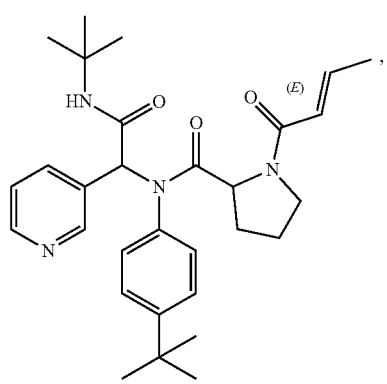
12
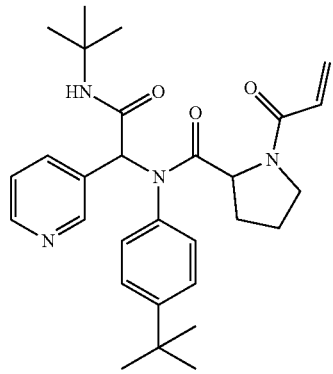
(L-proline), and
11
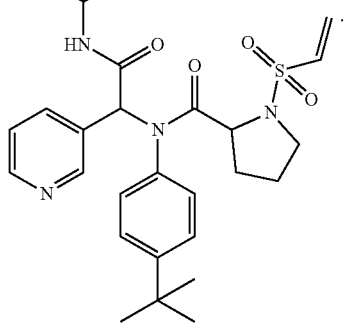
The compound of formula (I) can be
9
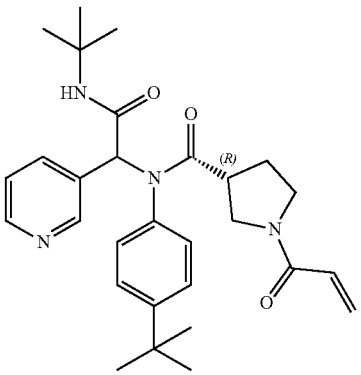
or
10
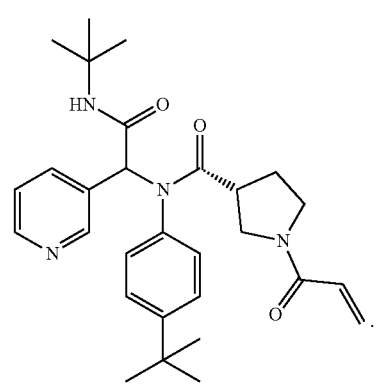

21
The compound of formula (I) can be or
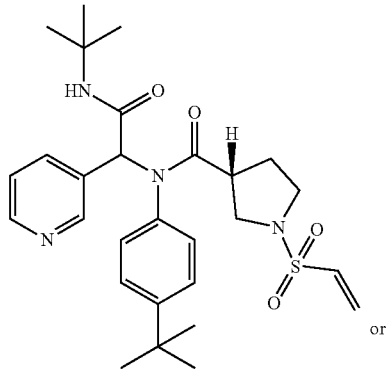
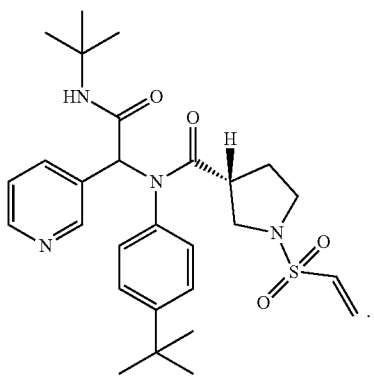
The compound of formula (I) can be (Down Isomer)
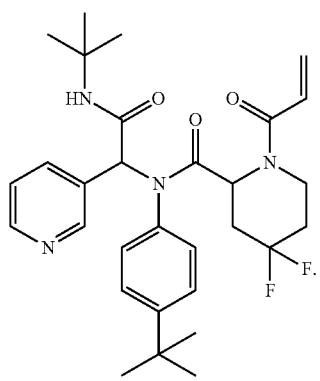
(Down Isomer)
22
The compound of formula (I) can be selected from:
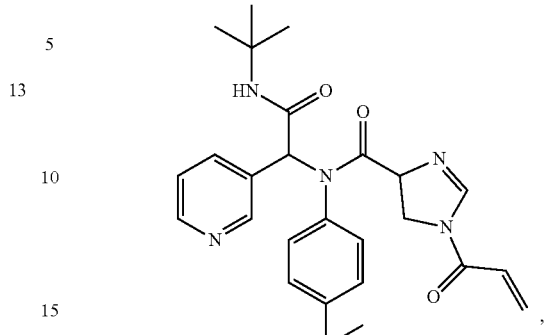
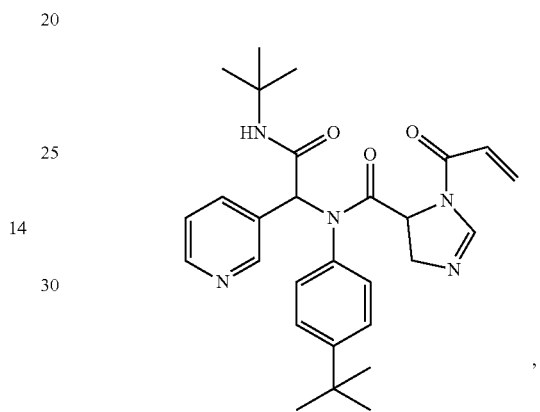
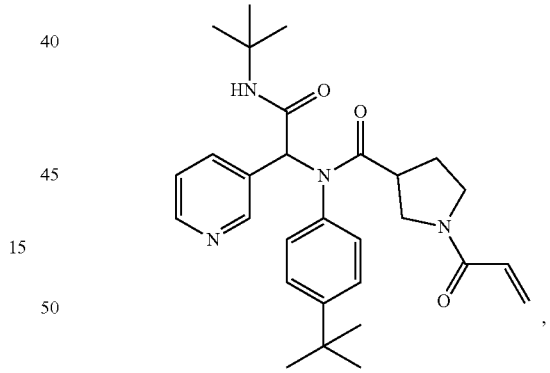
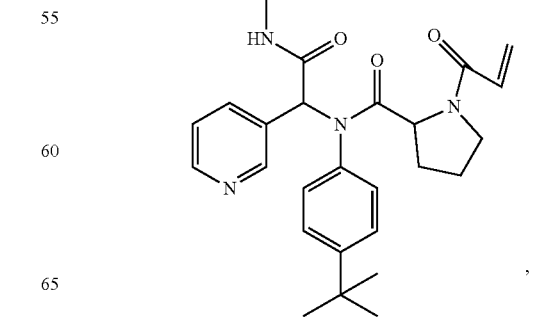

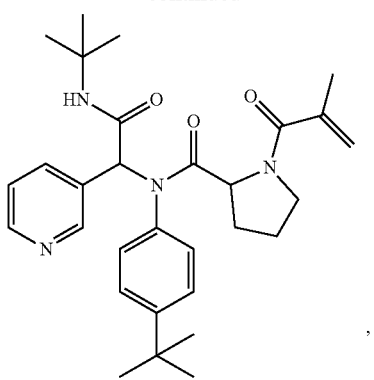
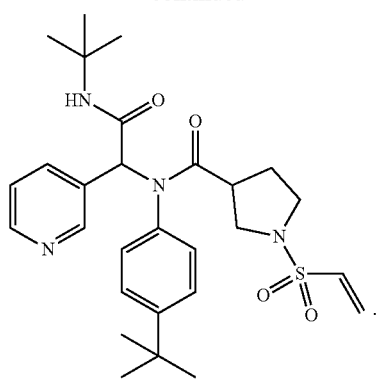
The compound of formula (I) can be selected from
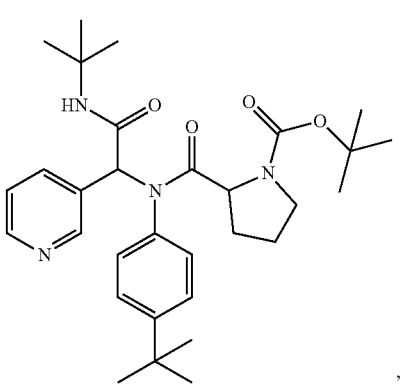
, and
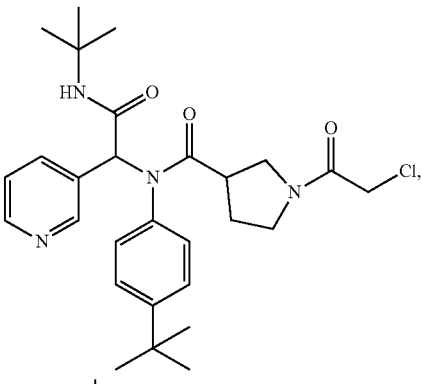
The compound of formula (I) can be selected from, and
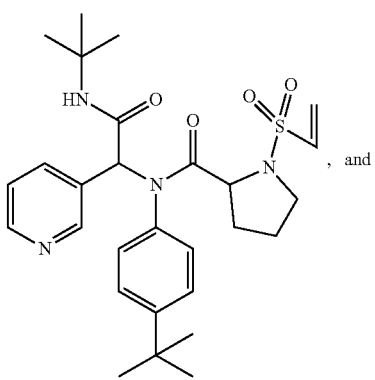
, and
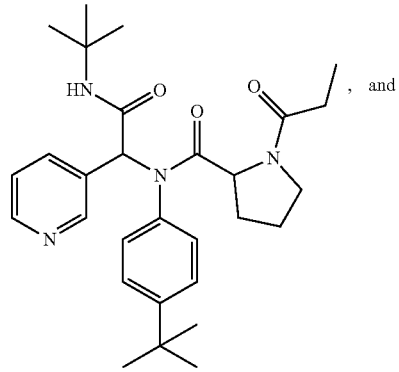
, and -continued
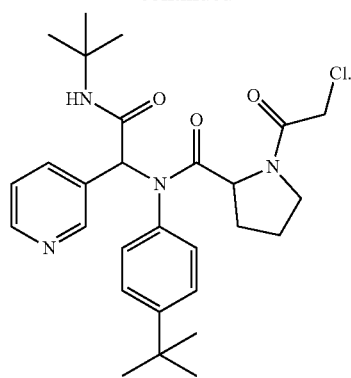
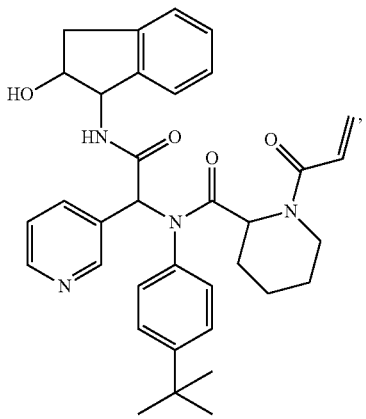
The compound of formula (I) can be selected from
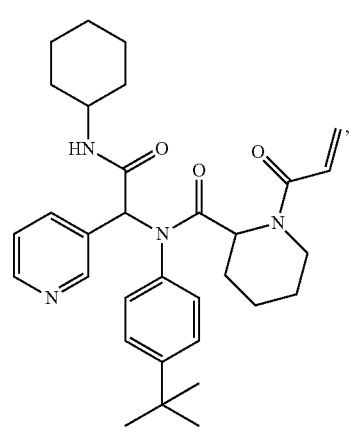
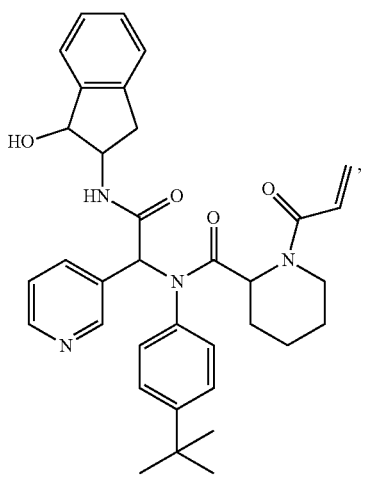
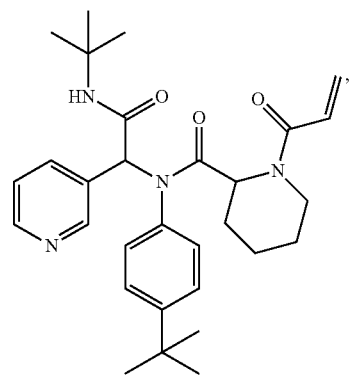
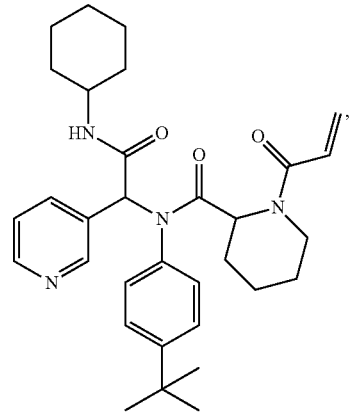
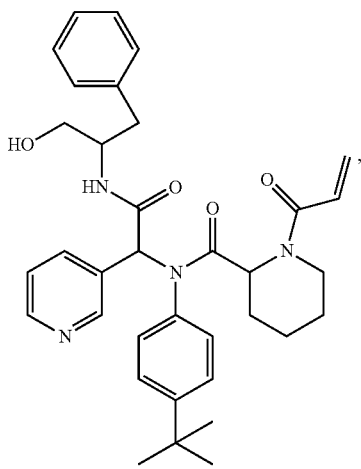

27
-continued
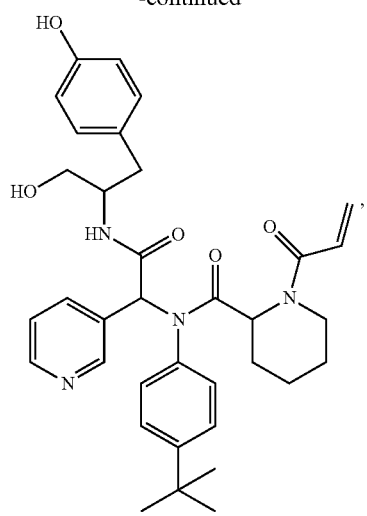
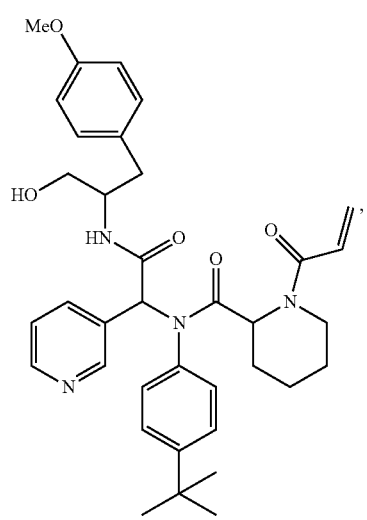
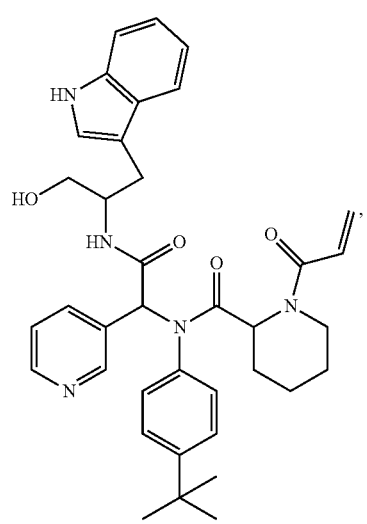
28
-continued
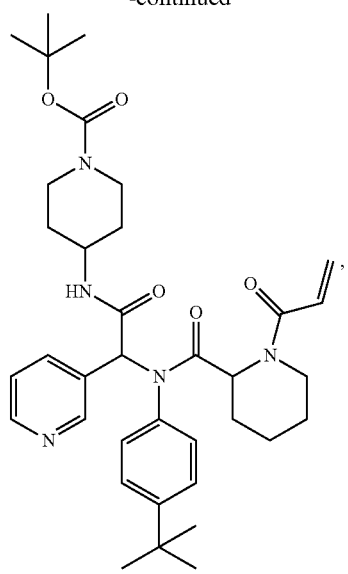
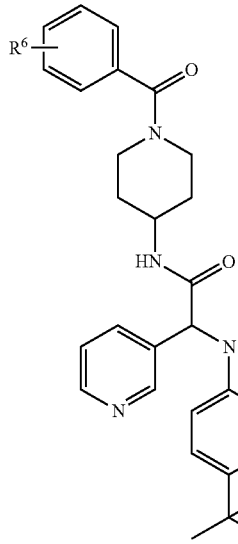
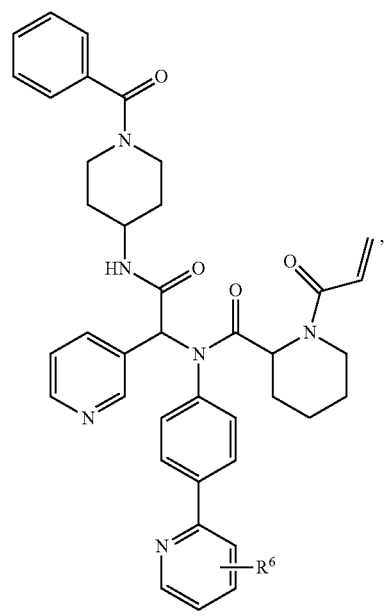

-continued
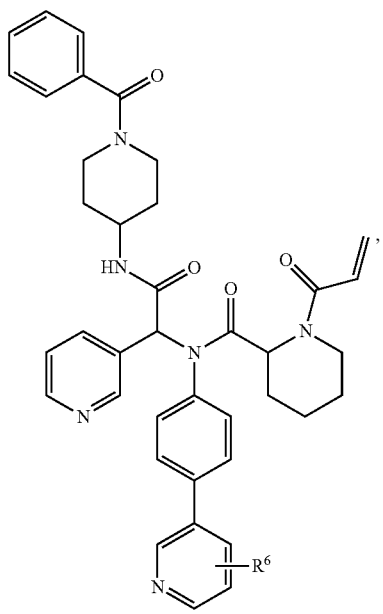
and
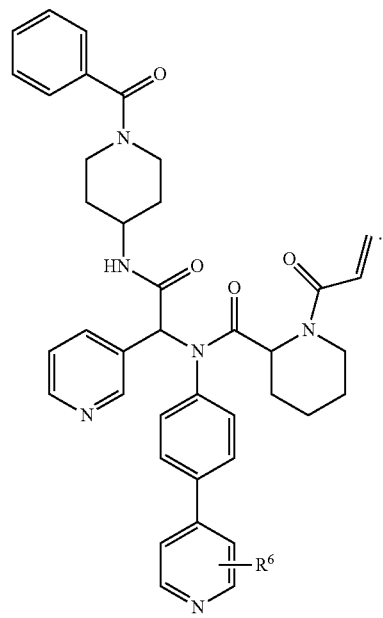
The compound of formula (I) can be selected from
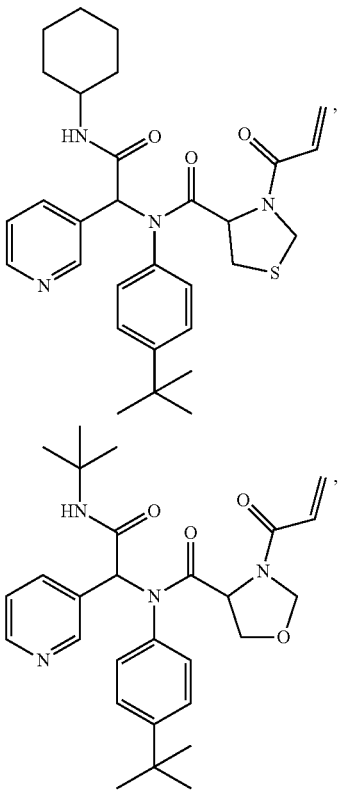
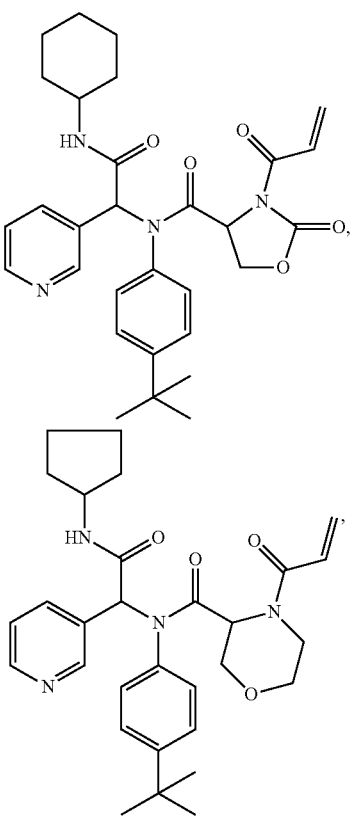

31
-continued
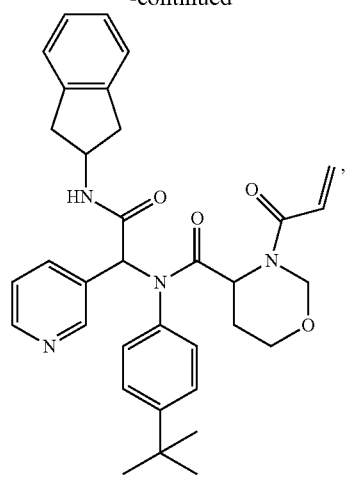
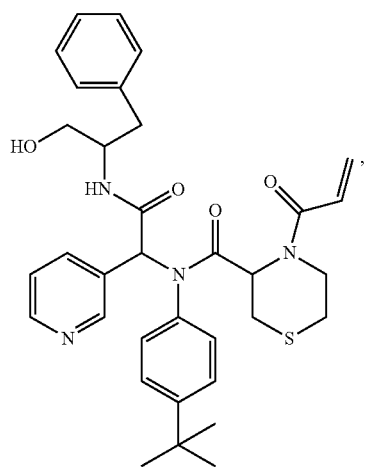
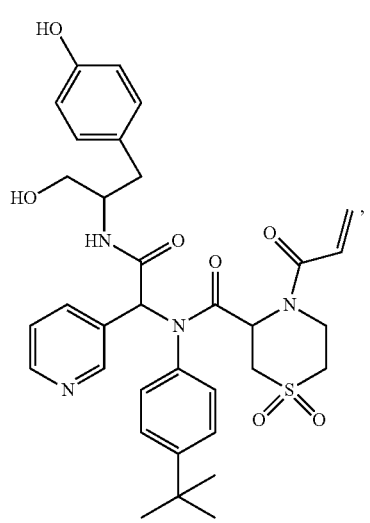
32
-continued
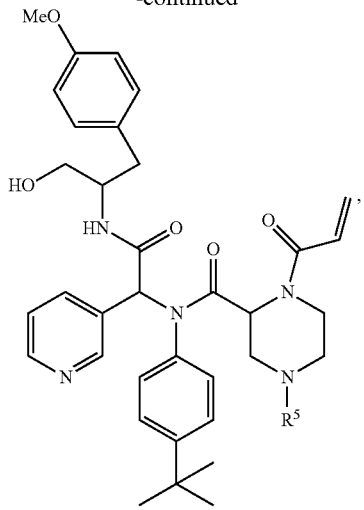
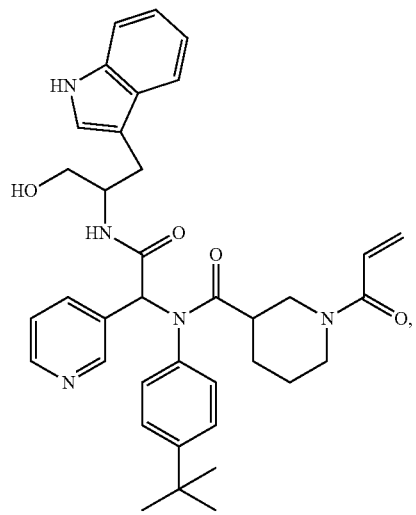
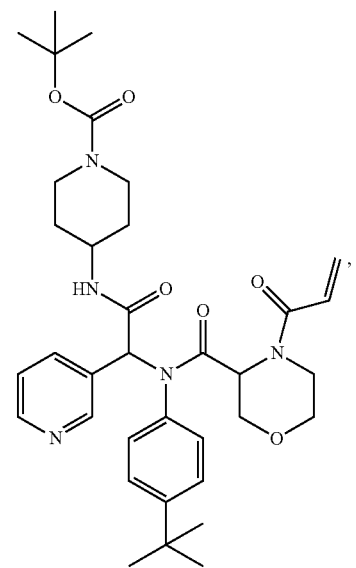

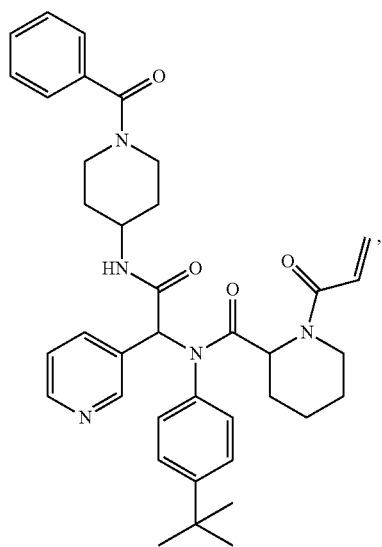
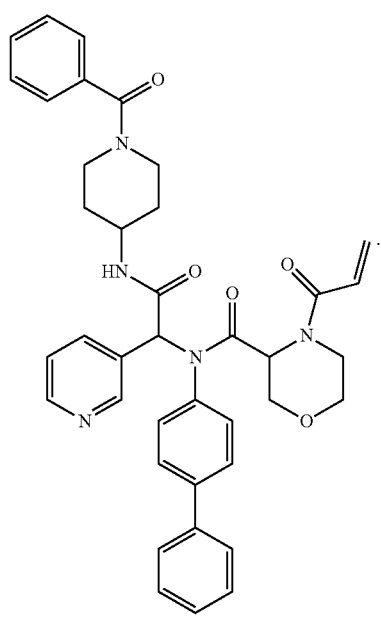
The compound of formula (I) can be selected from
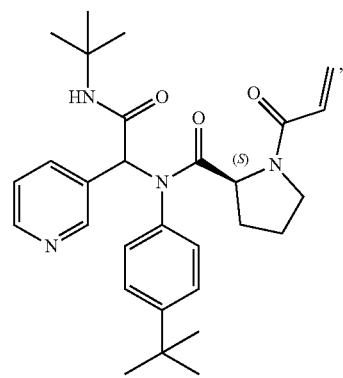
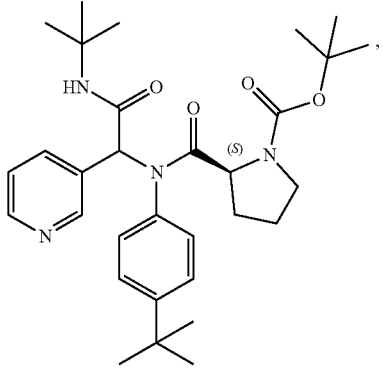
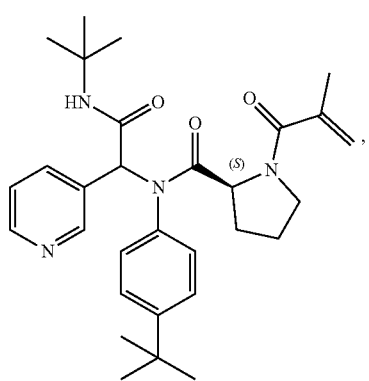
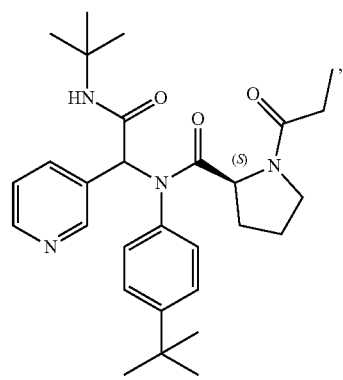
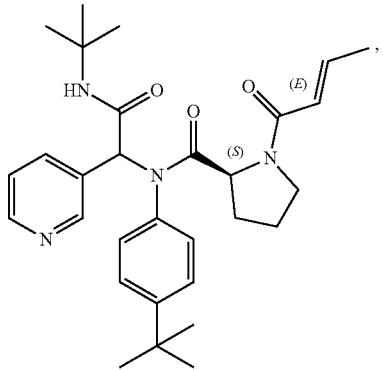

35
-continued
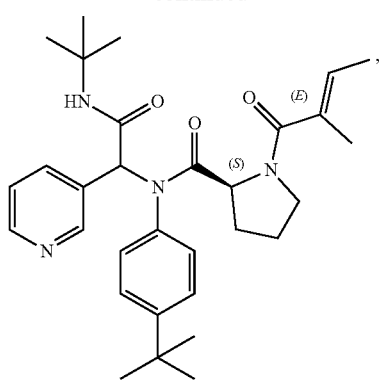
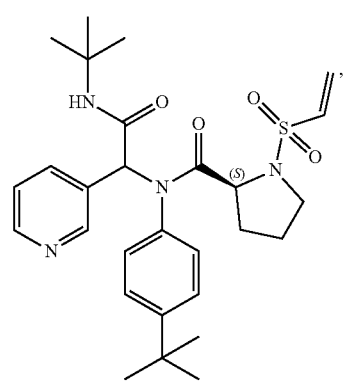
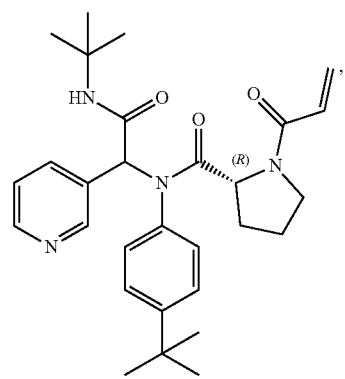
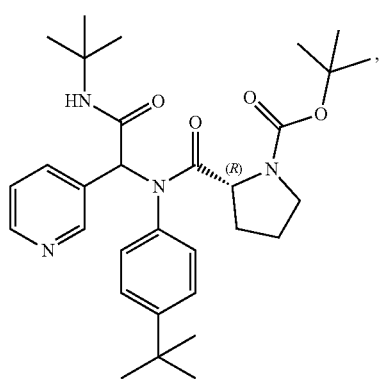
36
-continued
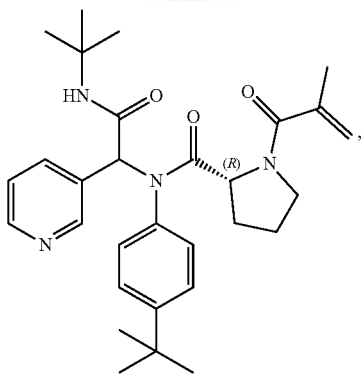
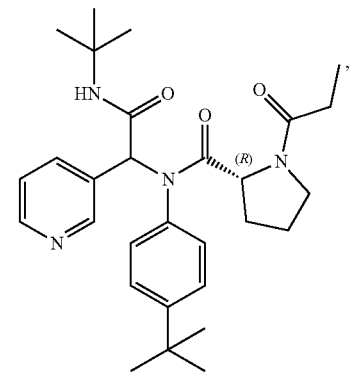
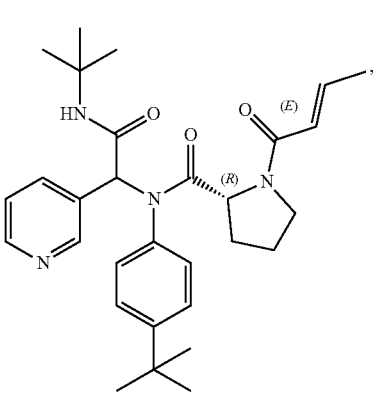
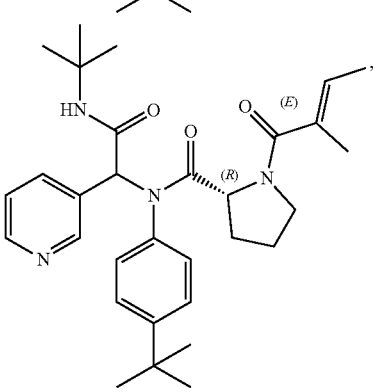

-continued
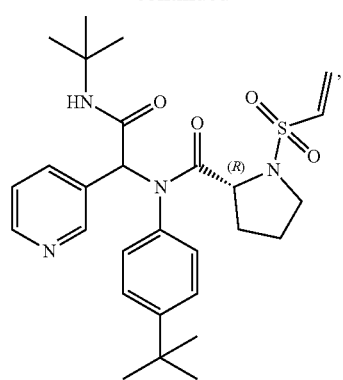
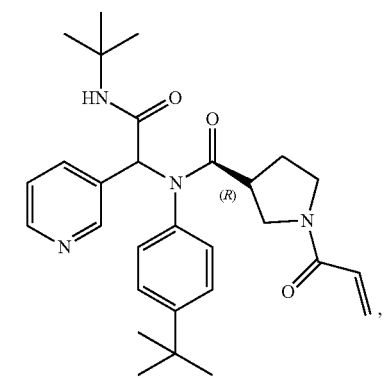
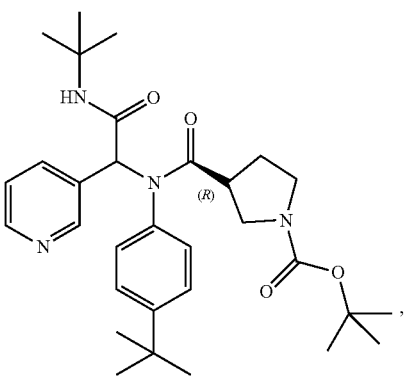
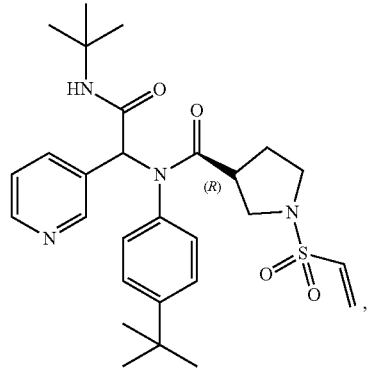
-continued
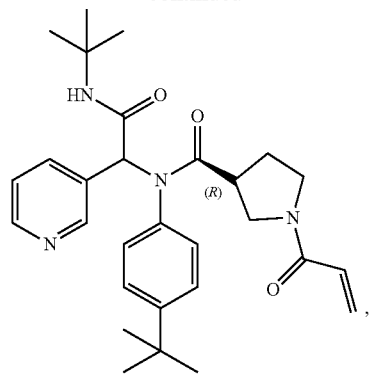
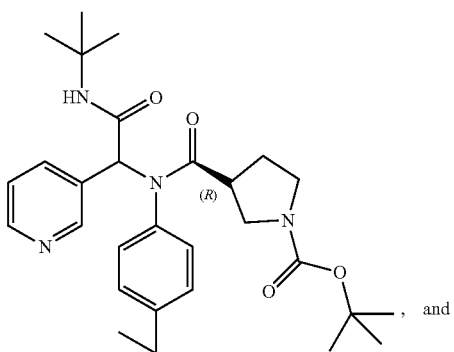, and
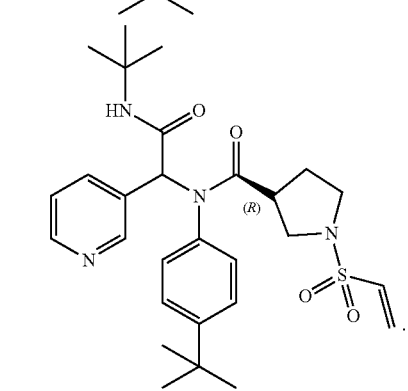
The compound of formula (I) can be selected from
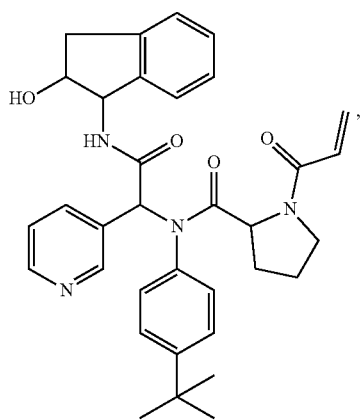

39
-continued
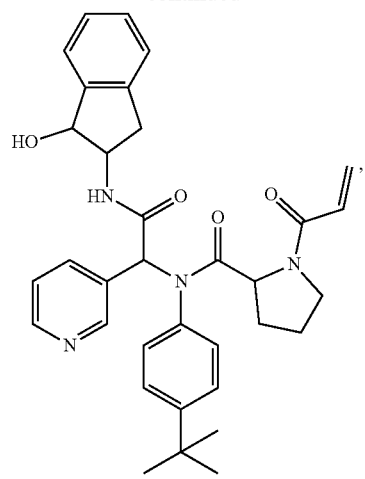
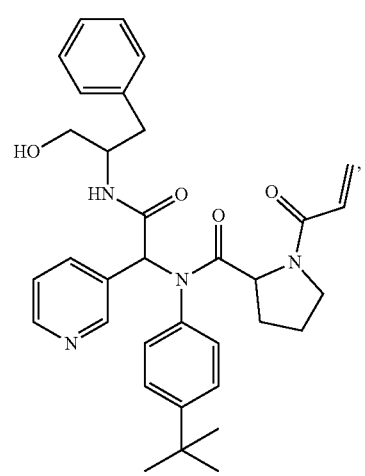
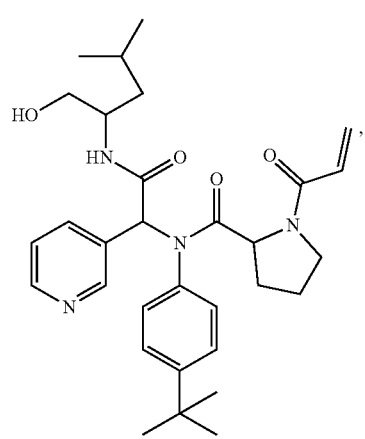
40
-continued
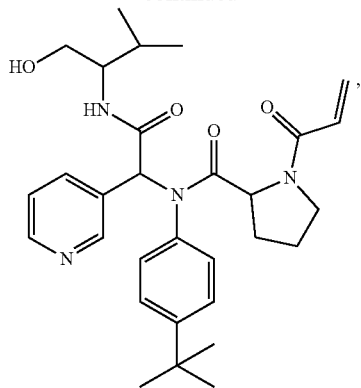
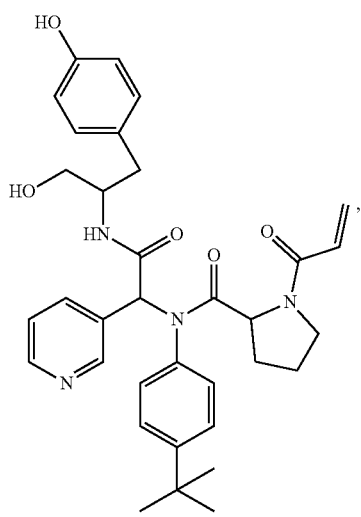

41
-continued
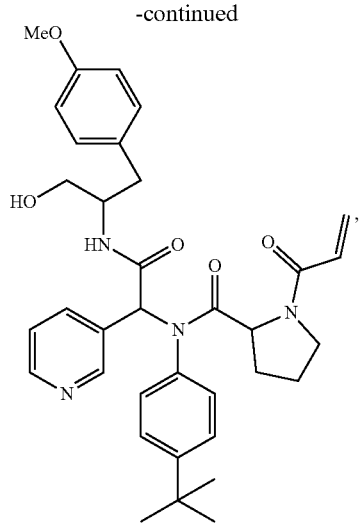
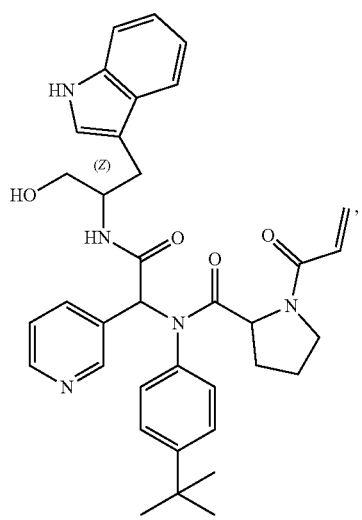
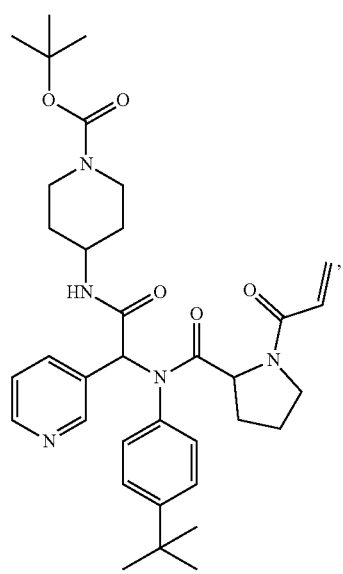
42
-continued
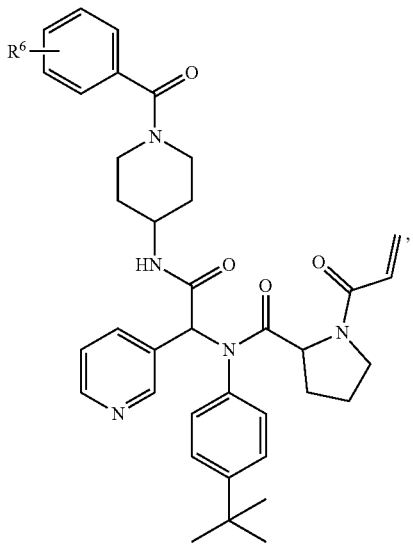
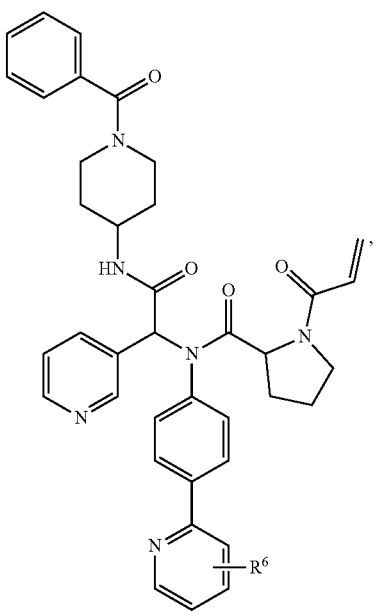

-continued

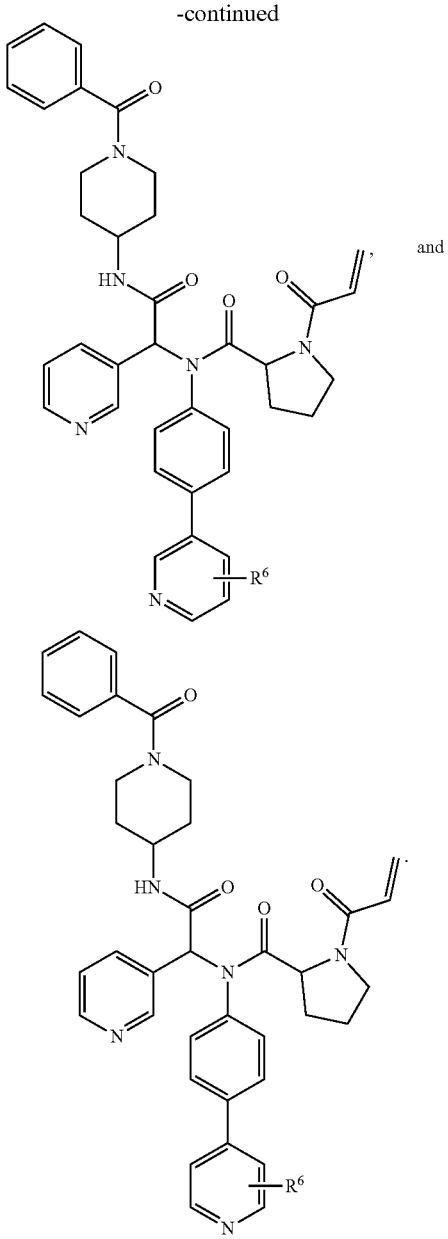

and

Methods of Treatment

The disclosure relates to a method of treating a severe acute respiratory syndrome comprising the step of administering to a subject in need thereof a therapeutically effective amount of any one of the aforementioned compounds or a pharmaceutical composition comprising same.

The severe acute respiratory syndrome can be due to a coronavirus infection. The coronavirus can be COVID-19.

Accordingly, the disclosure provides methods to treat a disease or disorder associated with SARS-CoV-2, comprising administering to a subject suffering therefrom a therapeutically effective amount of a compound or a pharmaceutical composition comprising same.

Pharmaceutical Compositions, Routes of Administration, and Dosing

Provided is a pharmaceutical composition comprising a compound and a pharmaceutically acceptable carrier. The pharmaceutical composition can comprise a plurality of compounds and a pharmaceutically acceptable carrier. The pharmaceutical composition can comprise a pharmaceutically acceptable salt of a compound.

A pharmaceutical composition can further comprise at least one additional pharmaceutically active agent. The at least one additional pharmaceutically active agent can be an agent useful in the treatment of ischemia-reperfusion injury.

Pharmaceutical compositions can be prepared by combining one or more compounds with a pharmaceutically acceptable carrier and, optionally, one or more additional pharmaceutically active agents.

As stated above, an "effective amount" refers to any amount that is sufficient to achieve a desired biological effect. Combined with the teachings provided herein, by choosing among the various active compounds and weighing factors such as potency, relative bioavailability, patient body weight, severity of adverse side-effects and mode of administration, an effective prophylactic or therapeutic treatment regimen can be planned which does not cause substantial unwanted toxicity and yet is effective to treat the particular subject. The effective amount for any particular application can vary depending on such factors as the disease or condition being treated, the particular compound being administered, the size of the subject, or the severity of the disease or condition. One of ordinary skill in the art can empirically determine the effective amount of a particular compound and/or other therapeutic agent without necessitating undue experimentation. A maximum dose can be used, that is, the highest safe dose according to some medical judgment. Multiple doses per day can be contemplated to achieve appropriate systemic levels of compounds. Appropriate systemic levels can be determined by, for example, measurement of the patient's peak or sustained plasma level of the drug. "Dose" and "dosage" are used interchangeably herein. "Dosage unit form," as used herein, refers to physically discrete units suited as unitary dosages for the mammalian subjects to be treated; each unit containing a predetermined quantity of active compound calculated to produce the desired therapeutic effect in association with the required pharmaceutical carrier. The specifications for the dosage unit forms of the invention are dictated by, and directly dependent on, the unique characteristics of the active compound and the particular therapeutic effect to be achieved, and the limitations inherent in the art of compounding such an active compound for the treatment of sensitivity in individuals. In therapeutic use for treatment of conditions in mammals (e.g., humans) for which the compounds or an appropriate pharmaceutical composition thereof are effective, the compounds can be administered in an effective amount.

Generally, daily oral doses of a compound are, for human subjects, from about 0.01 milligrams/kg per day to 1,000 milligrams/kg per day. Oral doses in the range of 0.5 to 50 milligrams/kg, in one or more administrations per day, can yield therapeutic results. Dosage can be adjusted appropriately to achieve desired drug levels, local or systemic, depending upon the mode of administration. For example, intravenous administration can vary from one order to several orders of magnitude lower dose per day. If the response in a subject is insufficient at such doses, even higher doses (or effective higher doses by a different, more localized delivery route) can be employed to the extent that patient tolerance permits. Multiple doses per day are contemplated to achieve appropriate systemic levels of the compound.

For any compound the therapeutically effective amount can be initially determined from animal models. A therapeutically effective dose can also be determined from human data for compounds which have been tested in humans and for compounds which are known to exhibit similar pharmacological activities, such as other related active agents. Higher doses can be required for parenteral administration. The applied dose can be adjusted based on the relative bioavailability and potency of the administered compound. Adjusting the dose to achieve maximal efficacy based on the methods described above and other methods as are well-known in the art is well within the capabilities of the ordinarily skilled artisan.

For clinical use, any compound can be administered in an amount equal or equivalent to 0.2-2,000 milligram (mg) of compound per kilogram (kg) of body weight of the subject per day. The compounds can be administered in a dose equal or equivalent to 2-2,000 mg of compound per kg body weight of the subject per day. The compounds can be administered in a dose equal or equivalent to 20-2,000 mg of compound per kg body weight of the subject per day. The compounds can be administered in a dose equal or equivalent to 50-2,000 mg of compound per kg body weight of the subject per day. The compounds can be administered in a dose equal or equivalent to 100-2,000 mg of compound per kg body weight of the subject per day. The compounds can be administered in a dose equal or equivalent to 200-2,000 mg of compound per kg body weight of the subject per day. Where a precursor or prodrug of a compound is to be administered, it is administered in an amount that is equivalent to, i.e., sufficient to deliver, the above-stated amounts of the compounds.

The formulations of the compounds can be administered to human subjects in therapeutically effective amounts. Typical dose ranges are from about 0.01 µg/kg to about 2 mg/kg of body weight per day. The dosage of drug to be administered is likely to depend on such variables as the type and extent of the disorder, the overall health status of the particular subject, the specific compound being administered, the excipients used to formulate the compound, and its route of administration. Routine experiments can be used to optimize the dose and dosing frequency for any particular compound.

The compounds can be administered at a concentration in the range from about 0.001 µg/kg to greater than about 500 mg/kg. For example, the concentration can be 0.001 µg/kg, 0.01 µg/kg, 0.05 µg/kg, 0.1 µg/kg, 0.5 µg/kg, 1.0 µg/kg, 10.0 µg/kg, 50.0 µg/kg, 100.0 µg/kg, 500 µg/kg, 1.0 mg/kg, 5.0 mg/kg, 10.0 mg/kg, 15.0 mg/kg, 20.0 mg/kg, 25.0 mg/kg, 30.0 mg/kg, 35.0 mg/kg, 40.0 mg/kg, 45.0 mg/kg, 50.0 mg/kg, 60.0 mg/kg, 70.0 mg/kg, 80.0 mg/kg, 90.0 mg/kg, 100.0 mg/kg, 150.0 mg/kg, 200.0 mg/kg, 250.0 mg/kg, 300.0 mg/kg, 350.0 mg/kg, 400.0 mg/kg, 450.0 mg/kg, to greater than about 500.0 mg/kg or any incremental value thereof. It is to be understood that all values and ranges between these values and ranges are meant to be encompassed.

The compounds can be administered at a dosage in the range from about 0.2 mg/kg/day to greater than about 100 mg/kg/day. For example, the dosage can be 0.2 mg/kg/day to 100 mg/kg/day, 0.2 mg/kg/day to 50 mg/kg/day, 0.2 mg/kg/day to 25 mg/kg/day, 0.2 mg/kg/day to 10 mg/kg/day, 0.2 mg/kg/day to 7.5 mg/kg/day, 0.2 mg/kg/day to 5 mg/kg/day, 0.25 mg/kg/day to 100 mg/kg/day, 0.25 mg/kg/day to 50 mg/kg/day, 0.25 mg/kg/day to 25 mg/kg/day, 0.25 mg/kg/day to 10 mg/kg/day, 0.25 mg/kg/day to 7.5 mg/kg/day, 0.25 mg/kg/day to 5 mg/kg/day, 0.5 mg/kg/day to 50 mg/kg/day, 0.5 mg/kg/day to 25 mg/kg/day, 0.5 mg/kg/day to 20 mg/kg/day, 0.5 mg/kg/day to 15 mg/kg/day, 0.5 mg/kg/day to 10 mg/kg/day, 0.5 mg/kg/day to 7.5 mg/kg/day, 0.5 mg/kg/day to 5 mg/kg/day, 0.75 mg/kg/day to 50 mg/kg/day, 0.75 mg/kg/day to 25 mg/kg/day, 0.75 mg/kg/day to 20 mg/kg/day, 0.75 mg/kg/day to 15 mg/kg/day, 0.75 mg/kg/day to 10 mg/kg/day, 0.75 mg/kg/day to 7.5 mg/kg/day, 0.75 mg/kg/day to 5 mg/kg/day, 1.0 mg/kg/day to 50 mg/kg/day, 1.0 mg/kg/day to 25 mg/kg/day, 1.0 mg/kg/day to 20 mg/kg/day, 1.0 mg/kg/day to 15 mg/kg/day, 1.0 mg/kg/day to 10 mg/kg/day, 1.0 mg/kg/day to 7.5 mg/kg/day, 1.0 mg/kg/day to 5 mg/kg/day, 2 mg/kg/day to 50 mg/kg/day, 2 mg/kg/day to 25 mg/kg/day, 2 mg/kg/day to 20 mg/kg/day, 2 mg/kg/day to 15 mg/kg/day, 2 mg/kg/day to 10 mg/kg/day, 2 mg/kg/day to 7.5 mg/kg/day, or 2 mg/kg/day to 5 mg/kg/day.

The compounds can be administered at a dosage in the range from about 0.25 mg/kg/day to about 25 mg/kg/day. For example, the dosage can be 0.25 mg/kg/day, 0.5 mg/kg/day, 0.75 mg/kg/day, 1.0 mg/kg/day, 1.25 mg/kg/day, 1.5 mg/kg/day, 1.75 mg/kg/day, 2.0 mg/kg/day, 2.25 mg/kg/day, 2.5 mg/kg/day, 2.75 mg/kg/day, 3.0 mg/kg/day, 3.25 mg/kg/day, 3.5 mg/kg/day, 3.75 mg/kg/day, 4.0 mg/kg/day, 4.25 mg/kg/day, 4.5 mg/kg/day, 4.75 mg/kg/day, 5 mg/kg/day, 5.5 mg/kg/day, 6.0 mg/kg/day, 6.5 mg/kg/day, 7.0 mg/kg/day, 7.5 mg/kg/day, 8.0 mg/kg/day, 8.5 mg/kg/day, 9.0 mg/kg/day, 9.5 mg/kg/day, 10 mg/kg/day, 11 mg/kg/day, 12 mg/kg/day, 13 mg/kg/day, 14 mg/kg/day, 15 mg/kg/day, 16 mg/kg/day, 17 mg/kg/day, 18 mg/kg/day, 19 mg/kg/day, 20 mg/kg/day, 21 mg/kg/day, 22 mg/kg/day, 23 mg/kg/day, 24 mg/kg/day, 25 mg/kg/day, 26 mg/kg/day, 27 mg/kg/day, 28 mg/kg/day, 29 mg/kg/day, 30 mg/kg/day, 31 mg/kg/day, 32 mg/kg/day, 33 mg/kg/day, 34 mg/kg/day, 35 mg/kg/day, 36 mg/kg/day, 37 mg/kg/day, 38 mg/kg/day, 39 mg/kg/day, 40 mg/kg/day, 41 mg/kg/day, 42 mg/kg/day, 43 mg/kg/day, 44 mg/kg/day, 45 mg/kg/day, 46 mg/kg/day, 47 mg/kg/day, 48 mg/kg/day, 49 mg/kg/day, or 50 mg/kg/day.

The compound or precursor thereof can be administered in concentrations that range from 0.01 µM to greater than or equal to 500 µM. For example, the dose can be 0.01 µM, 0.02 µM, 0.05 µM, 0.1 µM, 0.15 µM, 0.2 µM, 0.5 µM, 0.7 µM, 1.0 µM, 3.0 µM, 5.0 µM, 7.0 µM, 10.0 µM, 15.0 µM, 20.0 µM, 25.0 µM, 30.0 µM, 35.0 µM, 40.0 µM, 45.0 µM, 50.0 µM, 60.0 µM, 70.0 µM, 80.0 µM, 90.0 µM, 100.0 µM, 150.0 µM, 200.0 µM, 250.0 µM, 300.0 µM, 350.0 µM, 400.0 µM, 450.0 µM, to greater than about 500.0 µM or any incremental value thereof. It is to be understood that all values and ranges between these values and ranges are meant to be encompassed.

The compound or precursor thereof can be administered at concentrations that range from 0.10 µg/mL to 500.0 µg/mL. For example, the concentration can be 0.10 µg/mL, 0.50 µg/mL, 1 µg/mL, 2.0 µg/mL, 5.0 µg/mL, 10.0 µg/mL, 20 µg/mL, 25 µg/mL. 30 µg/mL, 35 µg/mL, 40 µg/mL, 45 µg/mL, 50 µg/mL, 60.0 µg/mL, 70.0 µg/mL, 80.0 µg/mL, 90.0 µg/mL, 100.0 µg/mL, 150.0 µg/mL, 200.0 µg/mL, 250.0 g/mL, 250.0 micro gram/mL, 300.0 µg/mL, 350.0 µg/mL, 400.0 µg/mL, 450.0 µg/mL, to greater than about 500.0 µg/mL or any incremental value thereof. It is to be understood that all values and ranges between these values and ranges are meant to be encompassed.

The formulations can be administered in pharmaceutically acceptable solutions, which can routinely contain pharmaceutically acceptable concentrations of salt, buffering agents, preservatives, compatible carriers, adjuvants, and optionally other therapeutic ingredients.

For use in therapy, an effective amount of the compound can be administered to a subject by any mode that delivers the compound to the desired surface. Administering a pharmaceutical composition can be accomplished by any means known to the skilled artisan. Routes of administration include, but are not limited to, intravenous, intramuscular, intraperitoneal, intravesical (urinary bladder), oral, subcutaneous, direct injection (for example, into a tumor or abscess), mucosal (e.g., topical to eye), inhalation, and topical.

For intravenous and other parenteral routes of administration, a compound can be formulated as a lyophilized preparation, as a lyophilized preparation of liposome-intercalated or -encapsulated active compound, as a lipid complex in aqueous suspension, or as a salt complex. Lyophilized formulations are generally reconstituted in suitable aqueous solution, e.g., in sterile water or saline, shortly prior to administration.

For oral administration, the compounds can be formulated readily by combining the active compound(s) with pharmaceutically acceptable carriers well-known in the art. Such carriers enable the compounds to be formulated as tablets, pills, dragees, capsules, liquids, gels, syrups, slurries, suspensions and the like, for oral ingestion by a subject to be treated. Pharmaceutical preparations for oral use can be obtained as solid excipient, optionally grinding a resulting mixture, and processing the mixture of granules, after adding suitable auxiliaries, if desired, to obtain tablets or dragee cores. Suitable excipients are fillers such as sugars, including lactose, sucrose, mannitol, or sorbitol; cellulose preparations such as, for example, maize starch, wheat starch, rice starch, potato starch, gelatin, gum tragacanth, methyl cellulose, hydroxypropylmethyl-cellulose, sodium carboxymethylcellulose, and/or polyvinylpyrrolidone (PVP). If desired, disintegrating agents can be added, such as the cross-linked polyvinyl pyrrolidone, agar, or alginic acid or a salt thereof such as sodium alginate. Optionally the oral formulations can also be formulated in saline solution or a buffer, e.g., EDTA, for neutralizing internal acid conditions or can be administered without any carriers.

Also contemplated are oral dosage forms of the compounds. The compounds can be chemically modified so that oral delivery of the derivative is efficacious. Generally, the chemical modification contemplated is the attachment of at least one moiety to the compound itself, where said moiety permits (a) inhibition of acid hydrolysis; and (b) uptake into the blood stream from the stomach or intestine. Also desired is the increase in overall stability of the compounds and increase in circulation time in the body. Examples of such moieties include polyethylene glycol, copolymers of ethylene glycol and propylene glycol, carboxymethyl cellulose, dextran, polyvinyl alcohol, polyvinyl pyrrolidone and polyproline. Abuchowski and Davis, "Soluble Polymer-Enzyme Adducts" In: Enzymes as Drugs, Hocenberg and Roberts, eds., Wiley-Interscience, New York, N.Y., pp. 367-383 (1981); Newmark et al., *J Appl Biochem* 4:185-189 (1982). Other polymers that could be used are poly-1,3-dioxolane and poly-1,3,6-tioxocane. For pharmaceutical usage, as indicated above, polyethylene glycol moieties are suitable.

The location of release of a compound can be the stomach, the small intestine (the duodenum, the jejunum, or the ileum), or the large intestine. One skilled in the art has available formulations which will not dissolve in the stomach yet will release the material in the duodenum or elsewhere in the intestine. The release can avoid the deleterious effects of the stomach environment, either by protection of the compound or by release of the compound beyond the stomach environment, such as in the intestine.

To ensure full gastric resistance a coating impermeable to at least pH 5.0 is essential. Examples of the more common inert ingredients that are used as enteric coatings are cellulose acetate trimellitate (CAT), hydroxypropylmethylcellulose phthalate (HPMCP), HPMCP 50, HPMCP 55, polyvinyl acetate phthalate (PVAP), Eudragit® L30D, Aquateric®, cellulose acetate phthalate (CAP), Eudragit® L, Eudragit® S, and shellac. These coatings can be used as mixed films.

A coating or mixture of coatings can also be used on tablets, which are not intended for protection against the stomach. This can include sugar coatings, or coatings which make the tablet easier to swallow. Capsules can consist of a hard shell (such as gelatin) for delivery of dry therapeutic (e.g., powder); for liquid forms, a soft gelatin shell can be used. The shell material of cachets could be thick starch or other edible paper. For pills, lozenges, molded tablets or tablet triturates, moist massing techniques can be used.

The therapeutic agent can be included in the formulation as fine multi-particulates in the form of granules or pellets of particle size about 1 mm. The formulation of the material for capsule administration could also be as a powder, lightly compressed plugs or even as tablets. The therapeutic could be prepared by compression.

Colorants and flavoring agents can all be included. For example, the compound can be formulated (such as by liposome or microsphere encapsulation) and then further contained within an edible product, such as a refrigerated beverage containing colorants and flavoring agents.

One can dilute or increase the volume of the therapeutic with an inert material. These diluents could include carbohydrates, especially mannitol, a-lactose, anhydrous lactose, cellulose, sucrose, modified dextrans and starch. Certain inorganic salts also can be used as fillers including calcium triphosphate, magnesium carbonate and sodium chloride. Some commercially available diluents are Fast-Flo®, Emdex®, STA-Rx 1500, Emcompress® and Avicel®.

Disintegrants can be included in the formulation of the therapeutic into a solid dosage form. Materials used as disintegrates include but are not limited to starch, including the commercial disintegrant based on starch, Explotab®. Sodium starch glycolate, AmberLite™ sodium carboxymethylcellulose, ultra-amylopectin, sodium alginate, gelatin, orange peel, acid carboxymethyl cellulose, natural sponge and bentonite can all be used. Another form of the disintegrant is the insoluble cationic exchange resin. Powdered gums can be used as disintegrants and as binders and these can include powdered gums such as agar, Karaya or tragacanth. Alginic acid and its sodium salt are also useful as disintegrants.

Binders can be used to hold the therapeutic agent together to form a hard tablet and include materials from natural products such as acacia, tragacanth, starch and gelatin. Others include methyl cellulose (MC), ethyl cellulose (EC) and carboxymethyl cellulose (CMC). Polyvinyl pyrrolidone (PVP) and hydroxypropylmethyl cellulose (HPMC) can both be used in alcoholic solutions to granulate the therapeutic agent.

An anti-frictional agent can be included in the formulation of the therapeutic to prevent sticking during the formulation process. Lubricants can be used as a layer between the therapeutic and the die wall, and these can include but are not limited to; stearic acid including its magnesium and calcium salts, polytetrafluoroethylene (PTFE), liquid paraffin, vegetable oils and waxes. Soluble lubricants can also be used such as sodium lauryl sulfate, magnesium lauryl sulfate, polyethylene glycol of various molecular weights, Carbowax 4000 and 6000.

Glidants that might improve the flow properties of the drug during formulation and to aid rearrangement during compression might be added. The glidants can include starch, talc, pyrogenic silica and hydrated silicoaluminate.

To aid dissolution of the therapeutic into the aqueous environment a surfactant might be added as a wetting agent. Surfactants can include anionic detergents such as sodium lauryl sulfate, dioctyl sodium sulfosuccinate and dioctyl sodium sulfonate. Cationic detergents which can be used and can include benzalkonium chloride and benzethonium chloride. Potential non-ionic detergents that could be included in the formulation as surfactants include lauromacrogol 400, polyoxyl 40 stearate, polyoxyethylene hydrogenated castor oil 10, 50 and 60, glycerol monostearate, polysorbate 40, 60, 65 and 80, sucrose fatty acid ester, methyl cellulose and carboxymethyl cellulose. These surfactants could be present in the formulation of the compound or derivative either alone or as a mixture in different ratios.

Pharmaceutical preparations which can be used orally include push-fit capsules made of gelatin, as well as soft, sealed capsules made of gelatin and a plasticizer, such as glycerol or sorbitol. The push-fit capsules can contain the active ingredients in admixture with filler such as lactose, binders such as starches, and/or lubricants such as talc or magnesium stearate and, optionally, stabilizers. In soft capsules, the active compounds can be dissolved or suspended in suitable liquids, such as fatty oils, liquid paraffin, or liquid polyethylene glycols. In addition, stabilizers can be added. Microspheres formulated for oral administration can also be used. Such microspheres have been well defined in the art. All formulations for oral administration should be in dosages suitable for such administration.

For buccal administration, the compositions can take the form of tablets or lozenges formulated in conventional manner.

For topical administration, the compound can be formulated as solutions, gels, ointments, creams, suspensions, etc. as are well-known in the art. Systemic formulations include those designed for administration by injection, e.g., subcutaneous, intravenous, intramuscular, intrathecal or intraperitoneal injection, as well as those designed for transdermal, transmucosal oral or pulmonary administration.

Nasal delivery of a pharmaceutical composition is also contemplated. Nasal delivery allows the passage of a pharmaceutical composition to the blood stream directly after administering the therapeutic product to the nose, without the necessity for deposition of the product in the lung. Formulations for nasal delivery include those with dextran or cyclodextran.

The compounds, when it is desirable to deliver them systemically, can be formulated for parenteral administration by injection, e.g., by bolus injection or continuous infusion. Formulations for injection can be presented in unit dosage form, e.g., in ampoules or in multi-dose containers, with an added preservative. The compositions can take such forms as suspensions, solutions or emulsions in oily or aqueous vehicles, and can contain formulatory agents such as suspending, stabilizing and/or dispersing agents.

Pharmaceutical formulations for parenteral administration include aqueous solutions of the active compounds in water-soluble form. Additionally, suspensions of the active compounds can be prepared as appropriate oily injection suspensions. Suitable lipophilic solvents or vehicles include fatty oils such as sesame oil, or synthetic fatty acid esters, such as ethyl oleate or triglycerides, or liposomes. Aqueous injection suspensions can contain substances which increase the viscosity of the suspension, such as sodium carboxymethylcellulose, sorbitol, or dextran. Optionally, the suspension can also contain suitable stabilizers or agents which increase the solubility of the compounds to allow for the preparation of highly concentrated solutions.

Alternatively, the active compounds can be in powder form for constitution with a suitable vehicle, e.g., sterile pyrogen-free water, before use.

The compounds can also be formulated in rectal or vaginal compositions such as suppositories or retention enemas, e.g., containing conventional suppository bases such as cocoa butter or other glycerides.

In addition to the formulations described above, a compound can also be formulated as a depot preparation. Such long-acting formulations can be formulated with suitable polymeric or hydrophobic materials (for example as an emulsion in an acceptable oil) or ion exchange resins, or as sparingly soluble derivatives, for example, as a sparingly soluble salt.

The pharmaceutical compositions also can comprise suitable solid or gel phase carriers or excipients. Examples of such carriers or excipients include but are not limited to calcium carbonate, calcium phosphate, various sugars, starches, cellulose derivatives, gelatin, and polymers such as polyethylene glycols.

Suitable liquid or solid pharmaceutical preparation forms are, for example, aqueous or saline solutions for inhalation, microencapsulated, encochleated, coated onto microscopic gold particles, contained in liposomes, nebulized, aerosols, pellets for implantation into the skin, or dried onto a sharp object to be scratched into the skin. The pharmaceutical compositions also include granules, powders, tablets, coated tablets, (micro)capsules, suppositories, syrups, emulsions, suspensions, creams, drops or preparations with protracted release of active compounds, in whose preparation excipients and additives and/or auxiliaries such as disintegrants, binders, coating agents, swelling agents, lubricants, flavorings, sweeteners or solubilizers are customarily used as described above. The pharmaceutical compositions are suitable for use in a variety of drug delivery systems. For a brief review of methods for drug delivery, see Langer R, *Science* 249:1527-1533 (1990).

The compound and optionally one or more other therapeutic agents can be administered per se (neat) or in the form of a pharmaceutically acceptable salt. When used in medicine the salts should be pharmaceutically acceptable, but non-pharmaceutically acceptable salts can conveniently be used to prepare pharmaceutically acceptable salts thereof. Such salts include, but are not limited to, those prepared from the following acids: hydrochloric, hydrobromic, sulphuric, nitric, phosphoric, maleic, acetic, salicylic, p-toluene sulphonic, tartaric, citric, methane sulphonic, formic, malonic, succinic, naphthalene-2-sulphonic, and benzene sulphonic. Also, such salts can be prepared as alkaline metal or alkaline earth salts, such as sodium, potassium or calcium salts of the carboxylic acid group.

Suitable buffering agents include acetic acid and a salt (1-2% w/v); citric acid and a salt (1-3% w/v); boric acid and a salt (0.5-2.5% w/v); and phosphoric acid and a salt (0.8-2% w/v). Suitable preservatives include benzalkonium chloride (0.003-0.03% w/v); chlorobutanol (0.3-0.9% w/v); parabens (0.01-0.25% w/v) and thimerosal (0.004-0.02% w/v).

Pharmaceutical compositions contain an effective amount of a compound as described herein and optionally one or more other therapeutic agents included in a pharmaceutically acceptable carrier. The term "pharmaceutically acceptable carrier" means one or more compatible solid or liquid fillers, diluents or encapsulating substances which are suitable for administration to a human or other vertebrate animal. The term "carrier" denotes an organic or inorganic ingredient, natural or synthetic, with which the active ingredient is combined to facilitate the application. The components of the pharmaceutical compositions also can be commingled with the compounds, and with each other, in a manner such that there is no interaction which would substantially impair the desired pharmaceutical efficiency.

The therapeutic agent(s), including specifically, but not limited to, a compound, can be provided in particles. "Particles" means nanoparticles or microparticles (or in some instances larger particles) which can consist in whole or in part of the compound or the other therapeutic agent(s) as described herein. The particles can contain the therapeutic agent(s) in a core surrounded by a coating, including, but not limited to, an enteric coating. The therapeutic agent(s) also can be dispersed throughout the particles. The therapeutic agent(s) also can be adsorbed into the particles. The particles can be of any order release kinetics, including zero-order release, first-order release, second-order release, delayed release, sustained release, immediate release, and any combination thereof, etc. The particle can include, in addition to the therapeutic agent(s), any of those materials routinely used in the art of pharmacy and medicine, including, but not limited to, erodible, non-erodible, biodegradable, or nonbiodegradable material or combinations thereof. The particles can be microcapsules which contain the compound in a solution or in a semi-solid state. The particles can be of virtually any shape.

Both non-biodegradable and biodegradable polymeric materials can be used in the manufacture of particles for delivering the therapeutic agent(s). Such polymers can be natural or synthetic polymers. The polymer is selected based on the period of time over which release is desired. Bioadhesive polymers of particular interest include bioerodible hydrogels described in Sawhney et al., Macromolecules 26:581-587 (1993), the teachings of which are specifically incorporated by reference herein. These include polyhyaluronic acids, casein, gelatin, glutin, polyanhydrides, polyacrylic acid, alginate, chitosan, poly(methyl methacrylates), poly(ethyl methacrylates), poly(butylmethacrylate), poly(isobutyl methacrylate), poly(hexylmethacrylate), poly(isodecyl methacrylate), poly(lauryl methacrylate), poly(phenyl methacrylate), poly(methyl acrylate), poly(isopropyl acrylate), poly(isobutyl acrylate), and poly(octadecyl acrylate).

The therapeutic agent(s) can be contained in controlled release systems. The term "controlled release" is intended to refer to any drug-containing formulation in which the manner and profile of drug release from the formulation are controlled. This refers to immediate as well as non-immediate release formulations, with non-immediate release formulations including but not limited to sustained release and delayed release formulations. The term "sustained release" (also referred to as "extended release") is used in its conventional sense to refer to a drug formulation that provides for gradual release of a drug over an extended period of time, and that can result in substantially constant blood levels of a drug over an extended time period. The term "delayed release" is used in its conventional sense to refer to a drug formulation in which there is a time delay between administration of the formulation and the release of the drug there from. "Delayed release" can or cannot involve gradual release of drug over an extended period of time, and thus can or cannot be "sustained release."

Use of a long-term sustained release implant can be particularly suitable for treatment of chronic conditions. "Long-term" release means that the implant is constructed and arranged to deliver therapeutic levels of the active ingredient for at least 7 days, and up to 30-60 days. Long-term sustained release implants are well-known to those of ordinary skill in the art and include some of the release systems described above.

Certain Definitions

For convenience, some terms employed in the specification, examples and appended claims are collected here. These definitions should be read in light of the remainder of the disclosure and understood as by a person of skill in the art. Unless defined otherwise, all technical and scientific terms used herein have the same meaning as commonly understood by a person of ordinary skill in the art.

The articles "a" and "an" are used herein to refer to one or to more than one (i.e., to at least one) of the grammatical object of the article. By way of example, "an element" means one element or more than one element.

The phrase "and/or," in the specification and in the claims, should be understood to mean "either or both" of the elements so conjoined, i.e., elements that are conjunctively present in some cases and disjunctively present in other cases. Multiple elements listed with "and/or" should be construed in the same fashion, i.e., "one or more" of the elements so conjoined. Other elements can optionally be present other than the elements specifically identified by the "and/or" clause, whether related or unrelated to those elements specifically identified. Thus, as a non-limiting example, a reference to "A and/or B," when used in conjunction with open-ended language such as "comprising" can refer, to A only (optionally including elements other than B); or to B only (optionally including elements other than A); or yet, to both A and B (optionally including other elements); etc.

In the specification and in the claims, "or" should be understood to have the same meaning as "and/or" as defined above. For example, when separating items in a list, "or" or "and/or" shall be interpreted as being inclusive, i.e., the inclusion of at least one, but also including more than one, of a number or list of elements, and, optionally, additional unlisted items. Only terms clearly indicated to the contrary, such as "only one of" or "exactly one of," or, when used in the claims, "consisting of," will refer to the inclusion of exactly one element of a number or list of elements. In general, the term "or" shall only be interpreted as indicating exclusive alternatives (i.e., "one or the other but not both") when preceded by terms of exclusivity, such as "either," "one of," "only one of," or "exactly one of." "Consisting essentially of," when used in the claims, shall have its ordinary meaning as used in the field of patent law.

In the specification and in the claims, the phrase "at least one," in reference to a list of one or more elements, should be understood to mean at least one element selected from any one or more of the elements in the list of elements, but not necessarily including at least one of each and every element specifically listed within the list of elements and not excluding any combinations of elements in the list of elements. This definition also allows that elements can optionally be present other than the elements specifically identified within the list of elements to which the phrase "at least one" refers, whether related or unrelated to those elements specifically identified. Thus, as a non-limiting example, "at least one of A and B" (or, equivalently, "at least one of A or B," or, equivalently "at least one of A and/or B") can refer, to at least one, optionally including more than one, A, with no B present (and optionally including elements other than B); or to at least one, optionally including more than one, B, with no A present (and optionally including elements other than A); or yet, to at least one, optionally including more than one, A, and at least one, optionally including more than one, B (and optionally including other elements); etc.

It should also be understood that, unless clearly indicated to the contrary, in any methods claimed herein that include more than one step or act, the order of the steps or acts of the method is not necessarily limited to the order in which the steps or acts of the method are recited.

In the claims, as well as in the specification above, all transitional phrases such as "comprising," "including," "carrying," "having," "containing," "involving," "holding," "composed of," and the like are to be understood to be open-ended, i.e., to mean including but not limited to.

The term "chiral" refers to molecules which have the property of non-superimposability of the mirror image partner, while the term "achiral" refers to molecules which are superimposable on their mirror image partner. "*" depicts certain chiral centers.

The term "stereoisomers" refers to compounds which have identical chemical constitution but differ with regard to the arrangement of the atoms or groups in space.

"Diastereomer" refers to a stereoisomer with two or more centers of chirality and whose molecules are not mirror images of one another. Diastereomers have different physical properties, e.g., melting points, boiling points, spectral properties, and reactivities. Mixtures of diastereomers may separate under high resolution analytical procedures such as electrophoresis and chromatography.

"Enantiomers" refer to two stereoisomers of a compound which are non-superimposable mirror images of one another.

Stereochemical definitions and conventions used herein generally follow S. P. Parker, Ed., McGraw-Hill Dictionary of Chemical Terms (1984) McGraw-Hill Book Company, New York; and Eliel, E. and Wilen, S., Stereochemistry of Organic Compounds, John Wiley & Sons, Inc., New York, 1994. The compounds of the invention may contain asymmetric or chiral centers, and therefore exist in different stereoisomeric forms. It is intended that all stereoisomeric forms of the compounds of the invention, including but not limited to, diastereomers, enantiomers and atropisomers, as well as mixtures thereof such as racemic mixtures, form part of the present invention. Many organic compounds exist in optically active forms, i.e., they have the ability to rotate the plane of plane-polarized light. In describing an optically active compound, the prefixes D and L, or R and S, are used to denote the absolute configuration of the molecule about its chiral center(s). The prefixes d and l or (+) and (−) are employed to designate the sign of rotation of plane-polarized light by the compound, with (−) or l meaning that the compound is levorotatory. A compound prefixed with (+) or d is dextrorotatory. For a given chemical structure, these stereoisomers are identical except that they are mirror images of one another. A specific stereoisomer may also be referred to as an enantiomer, and a mixture of such isomers is often called an enantiomeric mixture. A 50:50 mixture of enantiomers is referred to as a racemic mixture or a racemate, which may occur where there has been no stereoselection or stereospecificity in a chemical reaction or process. The terms "racemic mixture" and "racemate" refer to an equimolar mixture of two enantiomeric species, devoid of optical activity.

Various compounds contained in compositions can exist in particular geometric or stereoisomeric forms. The present disclosure contemplates all such compounds, including cis- and trans-isomers, R- and S-enantiomers, diastereomers, (D)-isomers, (L)-isomers, the racemic mixtures thereof, and other mixtures thereof, as falling within the scope of the disclosure. Additional asymmetric carbon atoms can be present in a substituent such as an alkyl group. All such isomers, as well as mixtures thereof, are intended to be included in this disclosure.

If, for instance, a particular enantiomer of compound is desired, it can be prepared by asymmetric synthesis, or by derivation with a chiral auxiliary, where the resulting diastereomeric mixture is separated and the auxiliary group cleaved to provide the pure desired enantiomers. Alternatively, where the molecule contains a basic functional group, such as amino, or an acidic functional group, such as carboxyl, diastereomeric salts are formed with an appropriate optically active acid or base, followed by resolution of the diastereomers thus formed by fractional crystallization or chromatographic means well-known in the art, and subsequent recovery of the pure enantiomers.

Structures depicted herein are also meant to include compounds that differ only in the presence of one or more isotopically enriched atoms. For example, compounds produced by the replacement of a hydrogen with deuterium or tritium, or of a carbon with a $^{13}C-$ or $^{14}C-$ enriched carbon are within the scope of this disclosure.

The phrase "pharmaceutically acceptable excipient" or "pharmaceutically acceptable carrier" means a pharmaceutically acceptable material, composition or vehicle, such as a liquid or solid filler, diluent, excipient, solvent or encapsulating material, involved in carrying or transporting the subject chemical from one organ or portion of the body to another organ or portion of the body. Each carrier must be "acceptable" in the sense of being compatible with the other ingredients of the formulation, not injurious to the patient, and substantially non-pyrogenic. Some examples of materials which can serve as pharmaceutically acceptable carriers include: (1) sugars, such as lactose, glucose, and sucrose; (2) starches, such as corn starch and potato starch; (3) cellulose, and its derivatives, such as sodium carboxymethyl cellulose, ethyl cellulose, and cellulose acetate; (4) powdered tragacanth; (5) malt; (6) gelatin; (7) talc; (8) excipients, such as cocoa butter and suppository waxes; (9) oils, such as peanut oil, cottonseed oil, safflower oil, sesame oil, olive oil, corn oil, and soybean oil; (10) glycols, such as propylene glycol; (11) polyols, such as glycerin, sorbitol, mannitol, and polyethylene glycol; (12) esters, such as ethyl oleate and ethyl laurate; (13) agar; (14) buffering agents, such as magnesium hydroxide and aluminum hydroxide; (15) alginic acid; (16) pyrogen-free water; (17) isotonic saline; (18) Ringer's solution; (19) ethyl alcohol; (20) phosphate buffer solutions; and (21) other non-toxic compatible substances employed in pharmaceutical formulations. Pharmaceutical compositions are non-pyrogenic, i.e., do not induce significant temperature elevations when administered to a patient.

The term "pharmaceutically acceptable salts" refers to the relatively non-toxic, inorganic and organic acid addition salts of the compound(s). These salts can be prepared in situ during the final isolation and purification of the compound(s), or by separately reacting a purified compound(s) in its free base form with a suitable organic or inorganic acid, and isolating the salt thus formed. Representative salts include the hydrobromide, hydrochloride, sulfate, bisulfate, phosphate, nitrate, acetate, valerate, oleate, palmitate, stearate, laurate, benzoate, lactate, phosphate, tosylate, citrate, maleate, fumarate, succinate, tartrate, naphthylate, mesylate, glucoheptonate, lactobionate, and laurylsulphonate salts, and the like. (See, for example, Berge et al. (1977) "Pharmaceutical Salts", J. Pharm. Sci. 66:1-19.)

In other cases, the compounds useful in the methods can contain one or more acidic functional groups and, thus, can form pharmaceutically acceptable salts with pharmaceutically acceptable bases. The term "pharmaceutically acceptable salts" in these instances refers to the relatively non-toxic inorganic and organic base addition salts of a compound(s). These salts can likewise be prepared in situ during the final isolation and purification of the compound(s), or by separately reacting the purified compound(s) in its free acid form with a suitable base, such as the hydroxide, carbonate, or bicarbonate of a pharmaceutically acceptable metal cation, with ammonia, or with a pharmaceutically acceptable organic primary, secondary, or tertiary amine. Representative alkali or alkaline earth salts include the lithium, sodium, potassium, calcium, magnesium, and aluminum salts, and the like. Representative organic amines useful for the formation of base addition salts include ethylamine, diethylamine, ethylenediamine, ethanolamine, diethanolamine, piperazine, and the like (see, for example, Berge et al., supra).

A "therapeutically effective amount" (or "effective amount") of a compound with respect to use in treatment, refers to an amount of the compound in a preparation which, when administered as part of a desired dosage regimen (to a mammal, such as a human) alleviates a symptom, ameliorates a condition, or slows the onset of disease conditions according to clinically acceptable standards for the disorder or condition to be treated or the cosmetic purpose, e.g., at a reasonable benefit/risk ratio applicable to any medical treatment.

The term "prophylactic or therapeutic" treatment is art-recognized and includes administration to the patient of one or more compound of the disclosure. If it is administered prior to clinical manifestation of the unwanted condition (e.g., disease or other unwanted state of the host animal) then the treatment is prophylactic, (i.e., it protects the host against developing the unwanted condition), whereas if it is administered after manifestation of the unwanted condition, the treatment is therapeutic, (i.e., it is intended to diminish, ameliorate, or stabilize the existing unwanted condition or side effects thereof).

The term "patient" or "subject" refers to a mammal suffering of a disease, disorder, or condition. A patient or subject can be a primate, canine, feline, or equine. A patient can ne subject is a bird. The bird can be a domesticated bird, such as chicken. The bird can be a fowl. A patient or subject can be a human.

An aliphatic chain comprises the classes of alkyl, alkenyl and alkynyl defined below. A straight aliphatic chain is limited to unbranched carbon chain moieties. The term "aliphatic group" refers to a straight chain, branched chain, or cyclic aliphatic hydrocarbon group and includes saturated and unsaturated aliphatic groups, such as an alkyl group, an alkenyl group, or an alkynyl group.

"Alkyl" refers to a fully saturated cyclic or acyclic, branched or unbranched carbon chain moiety having the number of carbon atoms specified, or up to 30 carbon atoms if no specification is made. For example, alkyl of 1 to 8 carbon atoms refers to moieties such as methyl, ethyl, propyl, butyl, pentyl, hexyl, heptyl, and octyl, and those moieties which are positional isomers of these moieties. Alkyl of 10 to 30 carbon atoms includes decyl, undecyl, dodecyl, tridecyl, tetradecyl, pentadecyl, hexadecyl, heptadecyl, octadecyl, nonadecyl, eicosyl, heneicosyl, docosyl, tricosyl and tetracosyl. A straight chain or branched chain alkyl can have 30 or fewer carbon atoms in its backbone (e.g., $C_1$-$C_{30}$ for straight chains, $C_3$-$C_{30}$ for branched chains), or 20 or fewer. Alkyl groups can be substituted or unsubstituted.

The term "alkylene" refers to an alkyl group having the specified number of carbons, for example from 2 to 12 carbon atoms, that contains two points of attachment to the rest of the compound on its longest carbon chain. Non-limiting examples of alkylene groups include methylene —($CH_2$)—, ethylene —($CH_2CH_2$)—, n-propylene —($CH_2CH_2CH_2$)—, isopropylene —($CH_2CH(CH_3)$)—, and the like. Alkylene groups can be cyclic or acyclic, branched or unbranched carbon chain moiety, and can be optionally substituted with one or more substituents.

"Cycloalkyl" means mono- or bicyclic or bridged or spirocyclic, or polycyclic saturated carbocyclic rings, each having from 3 to 12 carbon atoms. In various aspects, cycloalkyls have from 3-10 carbon atoms in their ring structure, or 3-6 carbons in the ring structure. Cycloalkyl groups can be substituted or unsubstituted.

Unless the number of carbons is otherwise specified, "lower alkyl," means an alkyl group, as defined above, but having from one to ten carbons, or from one to six carbon atoms in its backbone structure such as methyl, ethyl, n-propyl, isopropyl, n-butyl, isobutyl, sec-butyl, and tert-butyl. Likewise, "lower alkenyl" and "lower alkynyl" have similar chain lengths. A substituent designated herein as alkyl can be a lower alkyl.

"Alkenyl" refers to any cyclic or acyclic, branched or unbranched unsaturated carbon chain moiety having the number of carbon atoms specified, or up to 26 carbon atoms if no limitation on the number of carbon atoms is specified; and having one or more double bonds in the moiety. Alkenyl of 6 to 26 carbon atoms is exemplified by hexenyl, heptenyl, octenyl, nonenyl, decenyl, undecenyl, dodenyl, tridecenyl, tetradecenyl, pentadecenyl, hexadecenyl, heptadecenyl, octadecenyl, nonadecenyl, eicosenyl, heneicosoenyl, docosenyl, tricosenyl, and tetracosenyl, in their various isomeric forms, where the unsaturated bond(s) can be located anywhere in the moiety and can have either the (Z) or the (E) configuration about the double bond(s).

"Alkynyl" refers to hydrocarbyl moieties of the scope of alkenyl but having one or more triple bonds in the moiety.

The term "alkylthio" refers to an alkyl group, as defined above, having a sulfur moiety attached thereto. The "alkylthio" moiety can be represented by one of —(S)-alkyl, —(S)-alkenyl, —(S)-alkynyl, and —(S)—($CH_2$)$_m$-$R^1$, wherein m and $R^1$ are defined below. Representative alkylthio groups include methylthio, ethylthio, and the like. The terms "alkoxyl" or "alkoxy" refers to an alkyl group, as defined below, having an oxygen moiety attached thereto. Representative alkoxyl groups include methoxy, ethoxy, propoxy, tert-butoxy, and the like. An "ether" is two hydrocarbons covalently linked by an oxygen. Accordingly, the substituent of an alkyl that renders that alkyl an ether is or resembles an alkoxyl, such as can be represented by one of —O-alkyl, —O-alkenyl, —O-alkynyl, —O—($CH_2$)$_m$-$R_{10}$, where m and $R_{10}$ are described below.

The terms "amine" and "amino" are art-recognized and refer to both unsubstituted and substituted amines, e.g., a moiety that can be represented by the formulae:

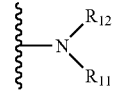

wherein R$_{11}$ and R$_{12}$ each independently represent a hydrogen, an alkyl, an alkenyl, —(CH$_2$)$_m$—R$_{10}$, or R$_{11}$ and R$_{12}$ taken together with the N atom to which they are attached complete a heterocycle having from 4 to 8 atoms in the ring structure; R$_{10}$ represents an alkenyl, aryl, cycloalkyl, a cycloalkenyl, a heterocyclyl, or a polycyclyl; and m is zero or an integer in the range of 1 to 8. In some instances, only one of R$_{11}$ or R$_{12}$ can be a carbonyl, e.g., R$_{11}$, R$_{12}$, and the nitrogen together do not form an imide. R$_{11}$ and R$_{12}$ each independently can represent a hydrogen, an alkyl, an alkenyl, or —(CH$_2$)$_m$—R$_{10}$. Thus, the term "alkylamine" means an amine group, as defined above, having a substituted or unsubstituted alkyl attached thereto, i.e., at least one of R$_{11}$ and R$_{12}$ is an alkyl group. An amino group or an alkylamine is basic, meaning it has a conjugate acid with a pK$_a$>7.00, i.e., the protonated forms of these functional groups have pK$_a$s relative to water above about 7.00.

The term "amide" refers to a group

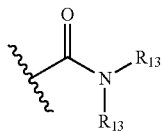

wherein each R$_{13}$ independently represent a hydrogen or hydrocarbyl group, or two R$_{13}$ are taken together with the N atom to which they are attached complete a heterocycle having from 4 to 8 atoms in the ring structure.

The term "aryl" includes 3- to 12-membered substituted or unsubstituted single-ring aromatic groups in which each atom of the ring is carbon (i.e., carbocyclic aryl) or where one or more atoms are heteroatoms (i.e., heteroaryl). In various aspects, aryl groups include 5- to 12-membered rings, or 6- to 10-membered rings. The term "aryl" also includes polycyclic ring systems having two or more cyclic rings in which two or more carbons are common to two adjoining rings wherein at least one of the rings is aromatic, e.g., the other cyclic rings can be cycloalkyls, cycloalkenyls, cycloalkynyls, aryls, heteroaryls, and/or heterocyclyls. Carbocyclic aryl groups include benzene, naphthalene, phenanthrene, phenol, aniline, and the like. Heteroaryl groups include substituted or unsubstituted aromatic 3- to 12-membered ring structures, 5- to 12-membered rings, or 5- to 10-membered rings, whose ring structures include one to four heteroatoms. Heteroaryl groups include, for example, pyrrole, furan, thiophene, imidazole, oxazole, thiazole, triazole, pyrazole, pyridine, pyrazine, pyridazine and pyrimidine, and the like. Aryl and heteroaryl can be monocyclic, bicyclic, or polycyclic. Each instance of an aryl group can be independently optionally substituted, i.e., unsubstituted (an "unsubstituted aryl") or substituted (a "substituted aryl") with one or more substituents; e.g., for instance from 1 to 5 substituents, 1 to 4 substituents, 1 to 3 substituents, 1 to 2 substituents or just 1 substituent. The aromatic ring can be substituted at one or more ring positions with one or more substituents, such as halogen, azide, alkyl, aryl, alkenyl, alkynyl, cycloalkyl, hydroxyl, alkoxyl, amino, nitro, sulfhydryl, imino, amido, phosphonate, phosphinate, carbonyl, carboxyl, silyl, ether, alkylthio, sulfonyl, sulfonamido, ketone, aldehyde, ester, heterocyclyl, aromatic or heteroaromatic moieties, fluoroalkyl (such as trifluromethyl), cyano, or the like. For example, the aryl group can be an unsubstituted C$_5$-C$_{12}$ aryl or a substituted C$_5$-C$_{10}$ aryl.

The term "halo", "halide", or "halogen" means halogen and includes, for example, and without being limited thereto, fluoro, chloro, bromo, iodo and the like, in both radioactive and non-radioactive forms. Halo can be selected from the group consisting of fluoro, chloro and bromo.

The terms "heterocyclyl" or "heterocyclic group" refer to 3- to 12-membered ring structures, 5- to 12-membered rings, or 5- to 10-membered rings, whose ring structures include one to four heteroatoms. Heterocycles can be monocyclic, bicyclic, spirocyclic, or polycyclic. Heterocycles can be saturated or unsaturated. Heterocyclyl groups include, for example, thiophene, thianthrene, furan, pyran, isobenzofuran, chromene, xanthene, phenoxathiin, pyrrole, imidazole, pyrazole, isothiazole, isoxazole, pyridine, pyrazine, pyrimidine, pyridazine, indolizine, isoindole, indole, indazole, purine, quinolizine, isoquinoline, quinoline, phthalazine, naphthyridine, quinoxaline, quinazoline, cinnoline, pteridine, carbazole, carboline, phenanthridine, acridine, pyrimidine, phenanthroline, phenazine, phenarsazine, phenothiazine, furazan, phenoxazine, pyrrolidine, oxolane, thiolane, oxazole, piperidine, piperazine, morpholine, lactones, lactams such as azetidinones and pyrrolidinones, sultams, sultones, and the like. The heterocyclic ring can be substituted at one or more positions with such substituents as described above, as for example, halogen, alkyl, aryl, alkenyl, alkynyl, cycloalkyl, hydroxyl, amino, nitro, sulfhydryl, imino, amido, phosphate, phosphonate, phosphinate, carbonyl, carboxyl, silyl, sulfamoyl, sulfinyl, ether, alkylthio, sulfonyl, ketone, aldehyde, ester, a heterocyclyl, an aromatic or heteroaromatic moiety, —CF$_3$, —CN, and the like.

The term "carbonyl" is art-recognized and includes such moieties as can be represented by the formula:

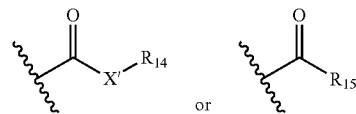

wherein X' is a bond or represents an oxygen, a nitrogen, or a sulfur, and R$_{14}$ represents a hydrogen, an alkyl, an alkenyl, —(CH$_2$)$_m$—R$_{10}$ or a pharmaceutically acceptable salt, R$_{15}$ represents a hydrogen, an alkyl, an alkenyl or —(CH$_2$)$_m$—R$_{10}$, where m and R$_{10}$ are as defined above. Where X' is an oxygen and R$_{14}$ or R$_{15}$ is not hydrogen, the formula represents an "ester." Where X' is an oxygen, and R$_{14}$ is as defined above, the moiety is referred to herein as a carboxyl group, and particularly when R$_{14}$ is a hydrogen, the formula represents a "carboxylic acid". Where X' is an oxygen, and R$_{15}$ is a hydrogen, the formula represents a "formate." In general, where the oxygen atom of the above formula is replaced by a sulfur, the formula represents a "thiocarbonyl" group. Where X' is a sulfur and R$_{14}$ or R$_{15}$ is not hydrogen, the formula represents a "thioester" group. Where X' is a sulfur and R$_{14}$ is a hydrogen, the formula represents a "thiocarboxylic acid" group. Where X' is a sulfur and R$_{15}$ is a hydrogen, the formula represents a "thioformate" group. On the other hand, where X' is a bond, and R$_{14}$ is not hydrogen, the above formula represents a "ketone" group. Where X' is a bond, and R$_{14}$ is a hydrogen, the above formula represents an "aldehyde" group.

The term "nitro" means —NO$_2$; the term "sulfhydryl" means —SH; the term "hydroxyl" means —OH; the term "sulfonyl" means —SO$_2$—; the term "azido" means —N$_3$; the term "cyano" means —CN; the term "isocyanato" means —NCO; the term "thiocyanato" means —SCN; the term "isothiocyanato" means —NCS; and the term "cyanato" means —OCN.

The definition of each expression, e.g., alkyl, m, n, etc., when it occurs more than once in any structure, is intended to be independent of its definition elsewhere in the same structure.

The term "substituted" refers to moieties having substituents replacing a hydrogen on one or more carbons of the backbone. It will be understood that "substitution" or "substituted with" includes the implicit proviso that such substitution is in accordance with permitted valence of the substituted atom and the substituent, and that the substitution results in a stable compound, e.g., which does not spontaneously undergo transformation such as by rearrangement, cyclization, elimination, etc. The term "substituted" is contemplated to include all permissible substituents of organic compounds. In a broad aspect, the permissible substituents include acyclic and cyclic, branched and unbranched, carbocyclic and heterocyclic, aromatic and non-aromatic substituents of organic compounds. The permissible substituents can be one or more and the same or different for appropriate organic compounds. Heteroatoms such as nitrogen can have hydrogen substituents and/or any permissible substituents of organic compounds described herein which satisfy the valences of the heteroatoms. Substituents can include any substituents described herein, for example, a halogen, a hydroxyl, a carbonyl (such as a carboxyl, an alkoxycarbonyl, a formyl, or an acyl), a thiocarbonyl (such as a thioester, a thioacetate, or a thioformate), an alkoxy, a phosphoryl, a phosphate, a phosphonate, a phosphinate, an amino, an amido, an amidine, an imine, a cyano, a nitro, an azido, a sulfhydryl, an alkylthio, a sulfate, a sulfonate, a sulfamoyl, a sulfonamido, a sulfonyl, a heterocyclyl, an aryl, or an aromatic or heteroaromatic moiety. The substituents on substituted alkyls can be selected from C$_{1-6}$ alkyl, C$_{3-6}$ cycloalkyl, halogen, carbonyl, cyano, or hydroxyl. The substituents on substituted alkyls can be selected from fluoro, carbonyl, cyano, or hydroxyl. It will be understood by those skilled in the art that substituents can themselves be substituted, if appropriate. Unless specifically stated as "unsubstituted," references to chemical moieties herein are understood to include substituted variants. For example, reference to an "aryl" group or moiety implicitly includes both substituted and unsubstituted variants.

The chemical elements are identified in accordance with the Periodic Table of the Elements, CAS version, Handbook of Chemistry and Physics, 67th Ed., 1986-87, inside cover.

All patents, patent application publications, journal articles, textbooks, and other publications mentioned in the specification are indicative of the level of skill of those in the art to which the disclosure pertains. All such publications are incorporated herein by reference to the same extent as if each individual publication were specifically and individually indicated to be incorporated by reference.

The invention illustratively described herein can be suitably practiced in the absence of any element(s) or limitation(s), which is/are not specifically disclosed herein. Thus, for example, each instance herein of any of the terms "comprising," "consisting essentially of," and "consisting of" can be replaced with either of the other two terms. Likewise, the singular forms "a," "an," and "the" include plural references unless the context clearly dictates otherwise. Thus, for example, references to "the method" includes one or more methods and/or steps of the type, which are described herein and/or which will become apparent to those ordinarily skilled in the art upon reading the disclosure.

The terms and expressions, which have been employed, are used as terms of description and not of limitation. In this regard, where certain terms are defined under "Definitions" and are otherwise defined, described, or discussed elsewhere in the "Detailed Description," all such definitions, descriptions, and discussions are intended to be attributed to such terms. There also is no intention in the use of such terms and expressions of excluding any equivalents of the features shown and described or portions thereof. Furthermore, while subheadings, e.g., "Definitions," are used in the "Detailed Description," such use is solely for ease of reference and is not intended to limit any disclosure made in one section to that section only; rather, any disclosure made under one subheading is intended to constitute a disclosure under each and every other subheading.

It will be understood by one of ordinary skill in the relevant arts that other suitable modifications and adaptations to the compositions and methods described herein are readily apparent from the description of the disclosure contained herein in view of information known to the ordinarily skilled artisan and can be made without departing from the scope of the disclosure. Having now described the present disclosure in detail, the same will be more clearly understood by reference to the following examples, which are included herewith for purposes of illustration only and are not intended to be limiting of the disclosure.

EXAMPLES

The present invention can be better understood by reference to the following examples which are offered by way of illustration. The present invention is not limited to the examples given herein.

The compounds described herein can be synthesized via the general synthetic procedure depicted in Scheme 1 herein.

General Scheme for 69492-02

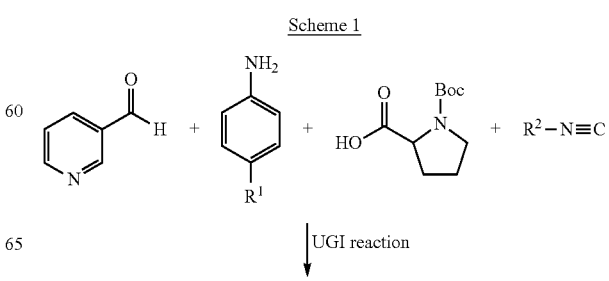

Scheme 1

-continued

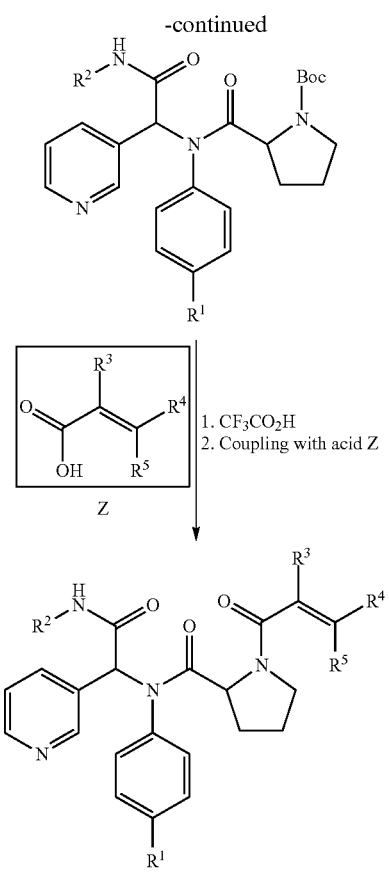

Synthetic Procedures

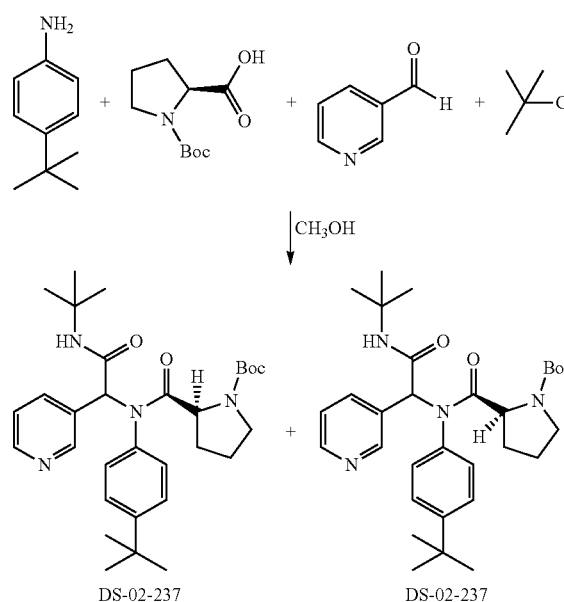

To the stirred solution of Boc-L-Proline (4.0 mmol, 1.0 eq) and 4-(tert-butyl)aniline (4.0 mmol, 1.0 eq) in methanol (5 mL), 3-Pyridinecarboxaldehyde (4.0 mmol, 1.0 eq) and trimethylacetonitrile (4.0 mmol, 1.0 eq) were added and the reaction mixture was stirred at the room temperature for 7 hours. The process of the reaction was monitored by TLC (eluent phase=ethyl acetate: hexane=80%). After completion of the reaction, its solvent was evaporated by rotary evaporator to give a residue. The residue was extracted with DCM (2×10 mL) and saturated solution of aqueous NaHCO$_3$(20 mL). The organic layer was dried over anhydrous Na$_2$SO$_4$ and concentrated under vacuum to give a residue. The crude compound was purified via silica gel flash column chromatography (SiO$_2$, 70% ethyl acetate: hexane) to afford the pure isomers.

Top Isomer: $^1$H NMR (400 MHz, Chloroform-D) 8.51-8.37 (m, 4H), 7.30 (t, J=6.6 Hz, 3H), 7.24-7.18 (m, 2H), 5.58 (s, 1H), 3.61 (dt, J=10.6, 6.6 Hz, 1H), 3.51-3.41 (m, 2H), 1.83-1.77 (m, 2H), 1.70 (td, J=13.6, 12.9, 6.8 Hz, 2H), 1.44 (s, 9H), 1.41 (s, 9H), 1.28 (s, 9H).

Down Isomer: $^1$H NMR (400 MHz, Chloroform-D) δ 8.51-8.47 (m, 1H), 8.42 (dd, J=4.8, 1.7 Hz, 1H), 8.36 (d, J=2.3 Hz, 1H), 7.28-7.16 (m, 3H), 7.10 (d, J=8.5 Hz, 2H), 7.04-6.96 (m, 1H), 6.40 (s, 1H), 4.11 (q, J=7.1 Hz, 1H), 3.52 (dt, J=10.3, 7.1 Hz, 1H), 3.40-3.32 (m, 1H), 1.86-1.78 (m, 2H), 1.70 (dq, J=11.8, 7.3 Hz, 2H), 1.46 (s, 9H), 1.46 (s, 9H), 1.27 (s, 9H).

As used herein, the term "top isomer" refers to an isomer that is higher (hence "top") on a thin layer chromatography (TLC) plate because it is less polar, whereas the term "down isomer" refers to an isomer that is lower (hence "down"), relative to the "top isomer," on a TLC plate.

Deprotection Boc from Isomers:

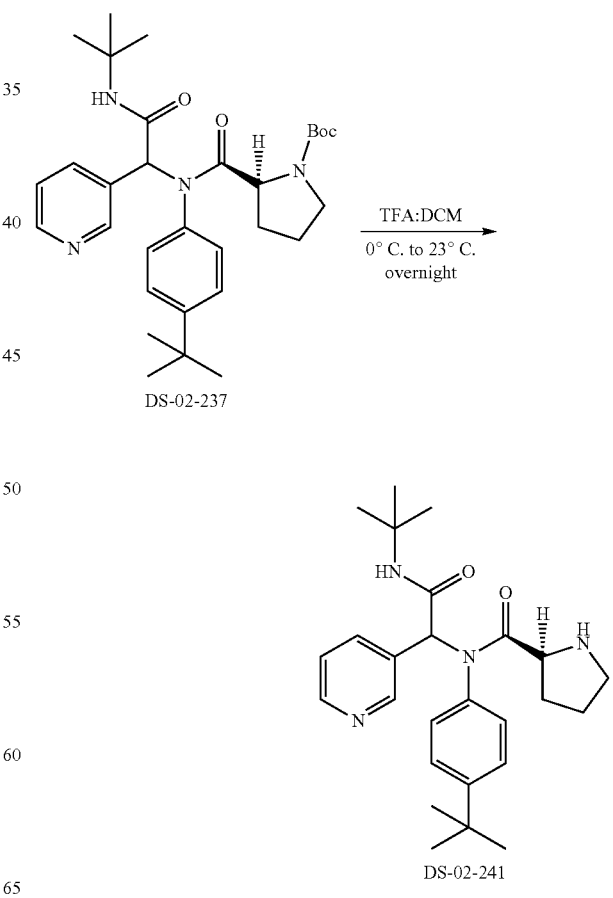

To the stirred solution of DS-02-237 (144 mg) in DCM (6 mL), TFA (2 mL) was added and the reaction mixture was stirred at 0° C. and then at room temperature for overnight. The process of the reaction was monitored by TLC (eluent phase=methanol: DCM=10%). After completion of the reaction, its solvent was evaporated by rotary evaporator to give a residue. The residue was extracted with ethyl acetate (2×10 mL) and saturated solution of aqueous NaHCO$_3$ (10 mL). The organic layer was dried over anhydrous Na$_2$SO$_4$ and concentrated under vacuum to give a residue. The crude compound was purified via silica gel flash column chromatography (SiO$_2$, 10% methanol: DCM) to afford the pure top isomer.

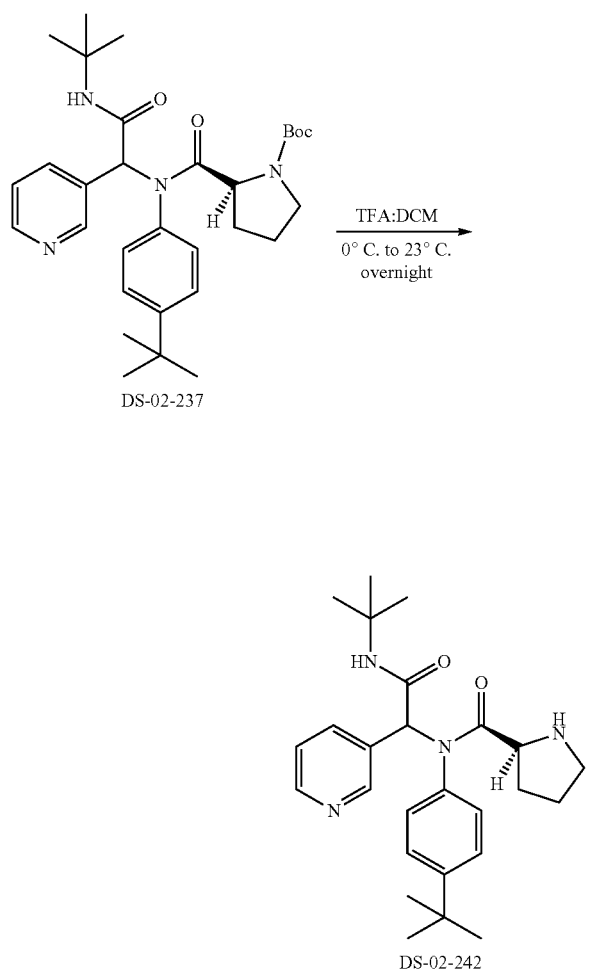

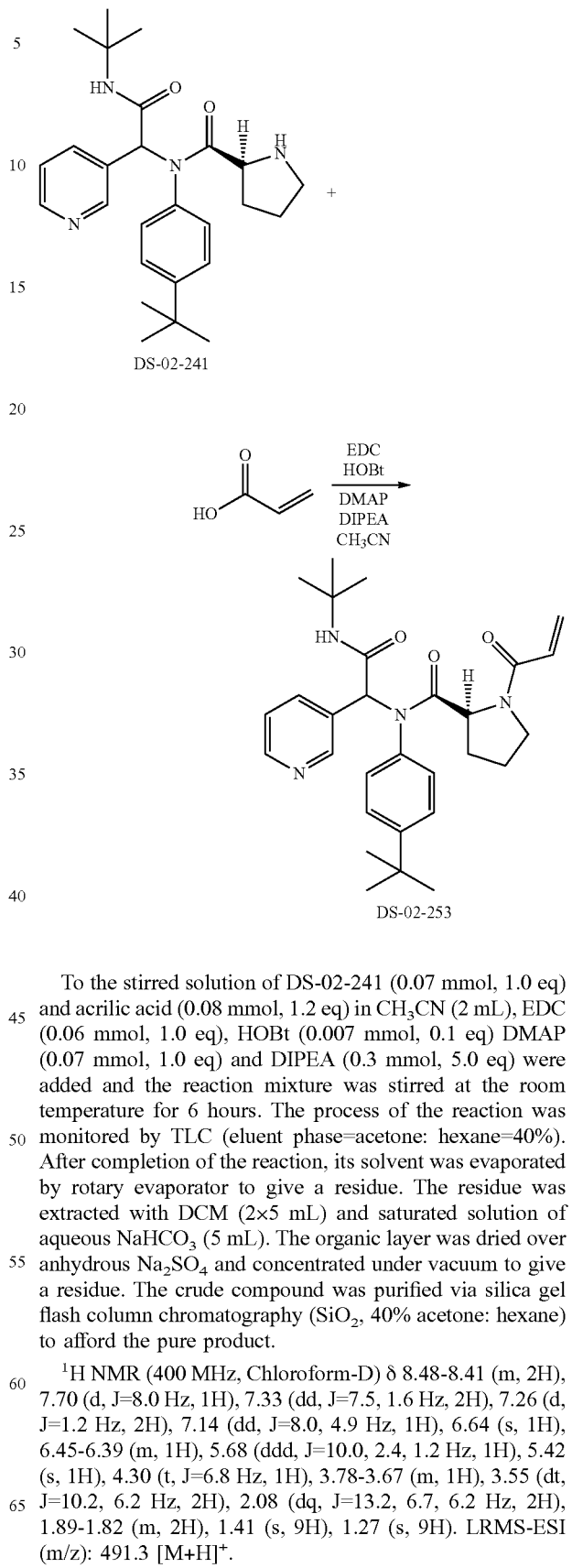

To the stirred solution of DS-02-237 (258 mg) in DCM (9 mL), TFA (3 mL) was added and the reaction mixture was stirred at 0° C. and then at room temperature for overnight. The process of the reaction was monitored by TLC (eluent phase=methanol: DCM=10%). After completion of the reaction, its solvent was evaporated by rotary evaporator to give a residue. The residue was extracted with ethyl acetate (2×10 mL) and saturated solution of aqueous NaHCO$_3$ (10 mL). The organic layer was dried over anhydrous Na$_2$SO$_4$ and concentrated under vacuum to give a residue. The crude compound was purified via silica gel flash column chromatography (SiO$_2$, 10% methanol: DCM) to afford the pure down isomer.

Synthesis of Amid Derivatives Via Two Isomers:

To the stirred solution of DS-02-241 (0.07 mmol, 1.0 eq) and acrilic acid (0.08 mmol, 1.2 eq) in CH$_3$CN (2 mL), EDC (0.06 mmol, 1.0 eq), HOBt (0.007 mmol, 0.1 eq) DMAP (0.07 mmol, 1.0 eq) and DIPEA (0.3 mmol, 5.0 eq) were added and the reaction mixture was stirred at the room temperature for 6 hours. The process of the reaction was monitored by TLC (eluent phase=acetone: hexane=40%). After completion of the reaction, its solvent was evaporated by rotary evaporator to give a residue. The residue was extracted with DCM (2×5 mL) and saturated solution of aqueous NaHCO$_3$ (5 mL). The organic layer was dried over anhydrous Na$_2$SO$_4$ and concentrated under vacuum to give a residue. The crude compound was purified via silica gel flash column chromatography (SiO$_2$, 40% acetone: hexane) to afford the pure product.

$^1$H NMR (400 MHz, Chloroform-D) δ 8.48-8.41 (m, 2H), 7.70 (d, J=8.0 Hz, 1H), 7.33 (dd, J=7.5, 1.6 Hz, 2H), 7.26 (d, J=1.2 Hz, 2H), 7.14 (dd, J=8.0, 4.9 Hz, 1H), 6.64 (s, 1H), 6.45-6.39 (m, 1H), 5.68 (ddd, J=10.0, 2.4, 1.2 Hz, 1H), 5.42 (s, 1H), 4.30 (t, J=6.8 Hz, 1H), 3.78-3.67 (m, 1H), 3.55 (dt, J=10.2, 6.2 Hz, 2H), 2.08 (dq, J=13.2, 6.7, 6.2 Hz, 2H), 1.89-1.82 (m, 2H), 1.41 (s, 9H), 1.27 (s, 9H). LRMS-ESI (m/z): 491.3 [M+H]$^+$.

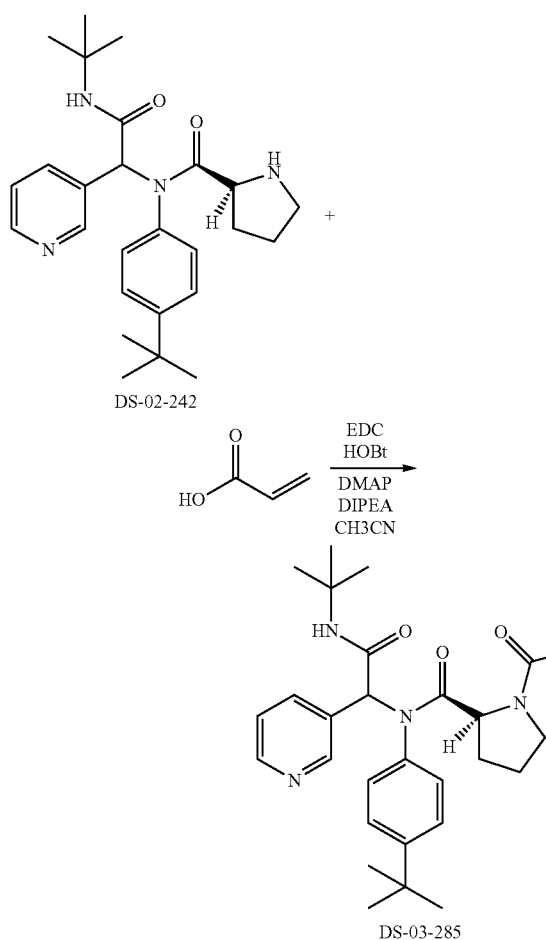

To the stirred solution of DS-02-242 (0.1 mmol, 1.0 eq) and acrilic acid (0.1 mmol, 1.2 eq) in CH₃CN (2 mL), EDC (0.1 mmol, 1.0 eq), HOBt (0.001 mmol, 0.1 eq) DMAP (0.1 mmol, 1.0 eq) and DIPEA (0.5 mmol, 5.0 eq) were added and the reaction mixture was stirred at the room temperature for 8 hours. The process of the reaction was monitored by TLC (eluent phase=acetone: hexane=40%). After completion of the reaction, its solvent was evaporated by rotary evaporator to give a residue. The residue was extracted with DCM (2×5 mL) and saturated solution of aqueous NaHCO₃(5 mL). The organic layer was dried over anhydrous Na₂SO₄ and concentrated under vacuum to give a residue. The crude compound was purified via silica gel flash column chromatography (SiO₂, 40% acetone: hexane) to afford the pure product.

¹H NMR (400 MHz, Chloroform-D) δ 8.44-8.33 (m, 3H), 7.30 (s, 1H), 7.22 (dt, J=8.0, 1.9 Hz, 2H), 7.02 (dd, J=8.0, 4.8 Hz, 2H), 6.36 (d, J=2.3 Hz, 1H), 6.17-6.07 (m, 1H), 5.89-5.82 (m, 1H), 5.70 (dd, J=10.0, 2.3 Hz, 1H), 4.21 (dd, J=7.6, 6.2 Hz, 1H), 3.77 (dt, J=9.7, 7.0 Hz, 1H), 3.65-3.56 (m, 2H), 1.90 (d, J=6.5 Hz, 2H), 1.72-1.68 (m, 2H), 1.48 (s, 9H), 1.25 (s, 9H). LRMS-ESI (m/z): 491.3 [M+H]⁺.

IC₅₀ Value (SARS-Cov-2 3CLpro Inhibition) Determination.

IC₅₀ values were determined for compounds that covalently inhibit SARS-CoV-2 3CLpro using a recently described assay (Ghosh, A. K. et al. Bioorg. Med. Chem. Lett. 2007, 17, 5876-5880) and data fitting methods that were derived from our previous work on SARS-CoV 3CLpro. The only differences were that pre-incubation of the enzyme with the compounds was 10 minutes instead of 20 minutes. In addition, the Morrison Equation was only used to determine the IC₅₀ value when they were below 1 μM.

Determination of Antiviral Activity.

Antiviral assay was carried out as described recently. (Hattori, S.-I et al. *Nat. Commun.* 2021, 12, 668; Hattori, S.-i. et al. *mBio* 2020, 11, e01833-20)

Cells were seeded in a 96-well plate (2×10⁴ cells/well) and incubated. After 24 h, virus was inoculated into cells at multiplicity of infection (MOI) of 0.05. After an additional 72 h, cell culture supernatants were harvested and viral RNA was extracted using a QIAamp viral RNA minikit (Qiagen, Hilden, Germany), and quantitative RT-PCR (RT-qPCR) was then performed using One Step PrimeScript III RT-qPCR mix (TaKaRa Bio, Shiga, Japan) following the instructions of the manufacturers. The primers and probe used for detecting SARS-CoV-2 envelope (6) were 5'-ACT TCT TTT TCT TGC TTT CGT GGT-3' (forward), 5'-GCA GCA GTA CGC ACA CAA TC-3' (reverse), and 5'-FAM-CTA GTT ACA CTA GCC ATC CTT ACT GC-black hole quencher 1 (BHQ1)-3' (probe). To determine the cytotoxicity of each compound, cells were seeded in a 96-well plate (2×10⁴ cells/well). One day later, various concentrations of each compound were added, and cells were incubated for additional 3 days. The 50% cytotoxic concentrations (CC₅₀) values were determined using the WST-8 assay and Cell Counting Kit-8 (Dojindo, Kumamoto, Japan).

TABLE 1

| | | |
|---|---|---|
| | Biological Evaluation | |
| Structure | IC₅₀ (SARS-CoV-2 3CLpro Inhibition) | ID₅₀ (Antiviral Data) |
| 1 | + | + |
| | + | + |

TABLE 1-continued

| | Biological Evaluation | |
|---|---|---|
| Structure | IC$_{50}$ (SARS-CoV-2 3CLpro Inhibition) | ID$_{50}$ (Antiviral Data) |
| 2 | + | + |
| 3 | + | + |
| 4 | + | + |
| 5 | | |
| 6 | ++ | + |
| 7 | +++ | + |
| 8 | ++ | + |

TABLE 1-continued

| Structure | IC50 (SARS-CoV-2 3CLpro Inhibition) | ID50 (Antiviral Data) |
|---|---|---|
| 9 | ++ | + |
| 10 | ++ | + |
| 11 | + | + |
| 12 | + | + |
| 13 | + | + |
| 14 | + | + |

TABLE 1-continued

Biological Evaluation

| Structure | IC$_{50}$ (SARS-CoV-2 3CLpro Inhibition) | ID$_{50}$ (Antiviral Data) |
|---|---|---|
| 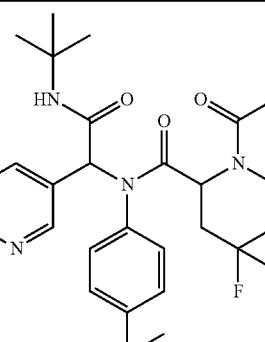<br>(Down Isomer)<br>15 | + | + |

Data Range Key:
0.1-999 nM ++++
1.0-10 μM +++
10.1-100 μM ++
>100 μM +

What is claimed:

1. A compound of Formula (IIIb) or (IIIc):

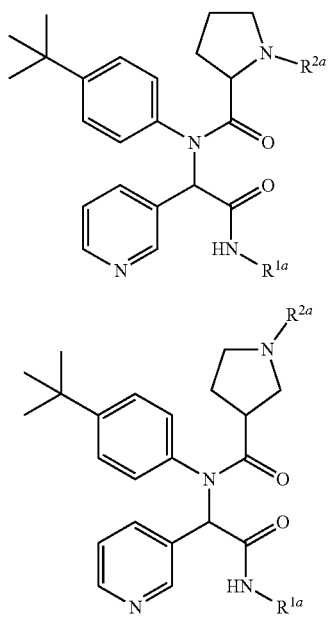

(IIIb)

(IIIc)

wherein:
R$^{1a}$ is alkyl; and
R$^{2a}$ is —C(O)alkyl, —C(O)alkenyl, or —S(O)$_2$-alkenyl;
or a pharmaceutically acceptable salt thereof.

2. The compound of claim 1, wherein R$^{1a}$ is t-butyl.

3. The compound of claim 1, wherein R$^{2a}$ is

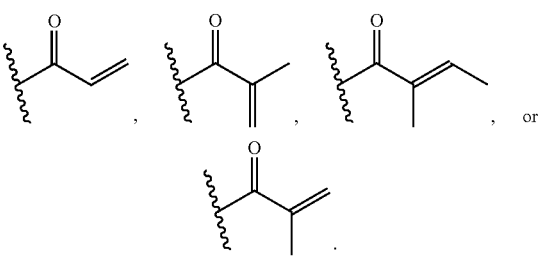

, or

4. The compound of claim 1, wherein R$^{2a}$ is

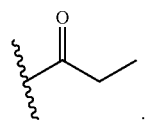

5. The compound of claim 1, wherein R$^{2a}$ is

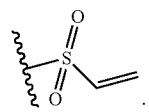

6. The compound of claim 1, wherein the compound of formula (IIIb) is selected from

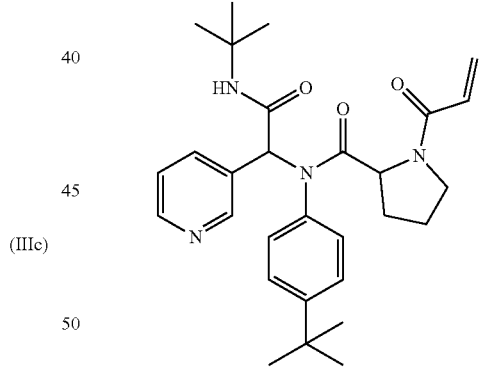

(D-proline),

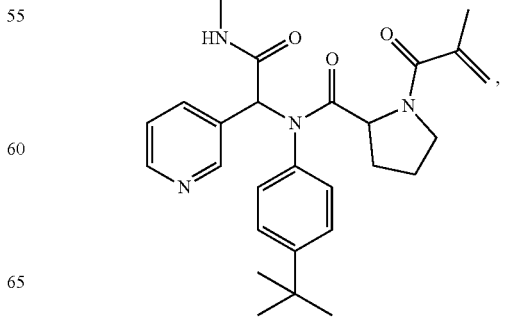

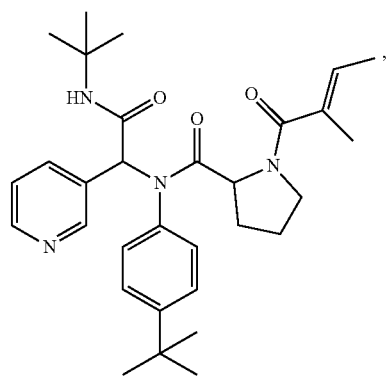
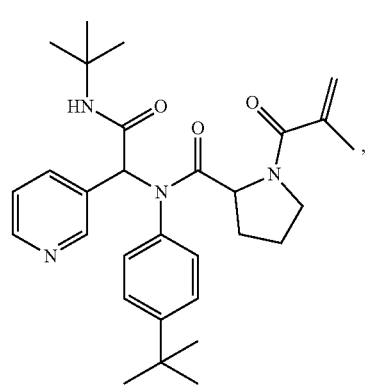
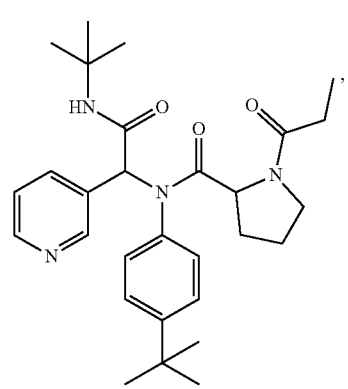
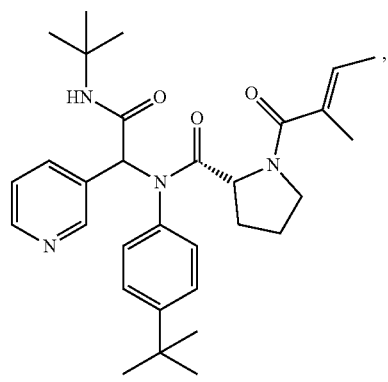
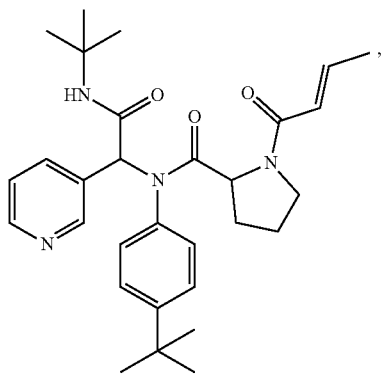
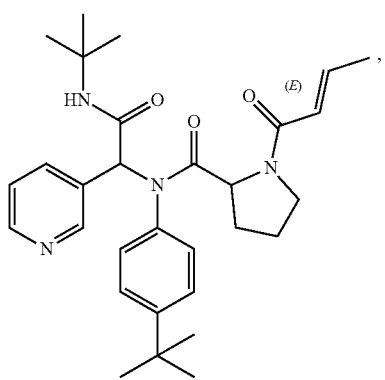
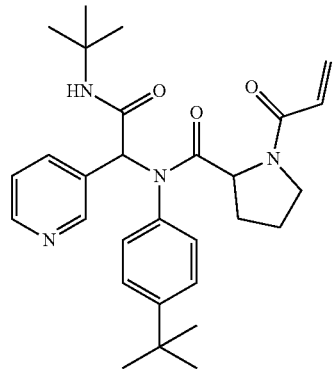 [SMILES: C=CC(=O)N1CCCC1C(=O)N(c1ccc(C(C)(C)C)cc1)C(C(=O)NC(C)(C)C)c1cccnc1]
(L-proline), and
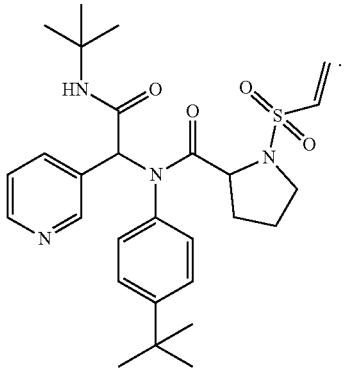

7. The compound of claim 1, wherein the compound of formula (IIIc) is
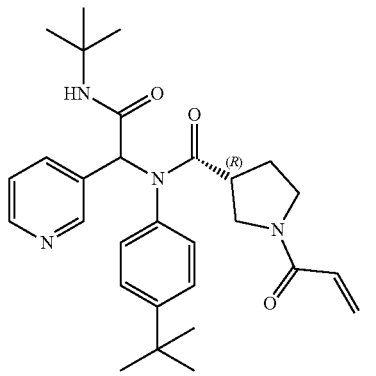
or
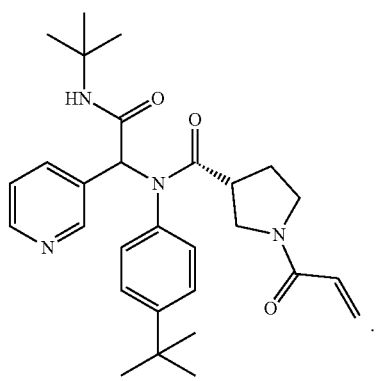
8. The compound of claim 1, wherein the compound of formula (IIIc) is
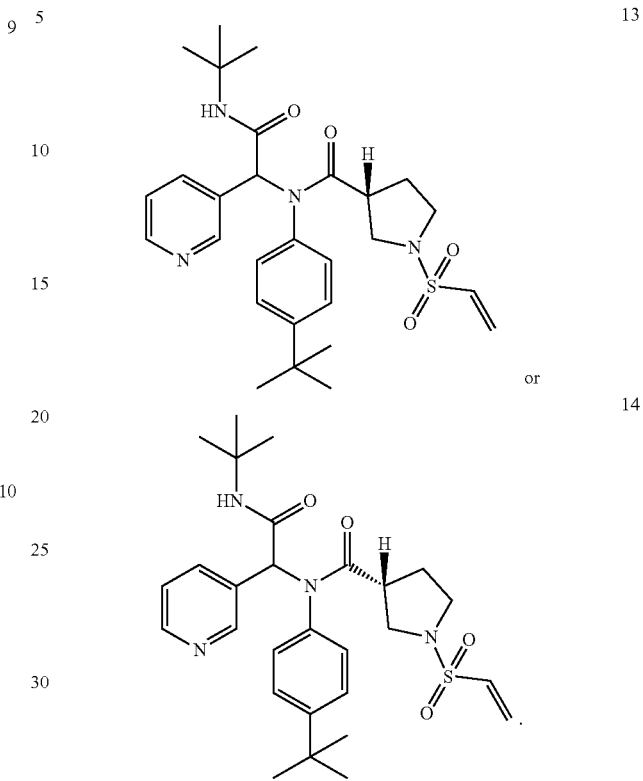
9. A pharmaceutical composition comprising a therapeutically effective amount of one or more compounds of claim 1 and at least one pharmaceutical acceptable carrier.
* * * * *